(12) United States Patent
Aradottir et al.

(10) Patent No.: US 11,462,313 B2
(45) Date of Patent: Oct. 4, 2022

(54) SYSTEMS AND METHODS FOR ADJUSTING A BASAL/BOLUS RATIO IN AN INSULIN REGIMEN

(71) Applicant: Novo Nordisk A/S, Bagsvaerd (DK)

(72) Inventors: Tinna Bjoerk Aradottir, Copenhagen (DK); Henrik Bengtsson, Taastrup (DK); Pete Brockmeier, Copenhagen V (DK); Jonas Kildegaard Pedersen, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 23 days.

(21) Appl. No.: 16/323,600

(22) PCT Filed: Aug. 14, 2017

(86) PCT No.: PCT/EP2017/070585
§ 371 (c)(1),
(2) Date: Feb. 6, 2019

(87) PCT Pub. No.: WO2018/033514
PCT Pub. Date: Feb. 22, 2018

(65) Prior Publication Data
US 2019/0164641 A1 May 30, 2019

(30) Foreign Application Priority Data

Aug. 17, 2016 (EP) .................................... 16184451

(51) Int. Cl.
*G16H 20/17* (2018.01)
*G16H 50/70* (2018.01)
(Continued)

(52) U.S. Cl.
CPC ............ *G16H 20/17* (2018.01); *A61B 5/4836* (2013.01); *G16H 10/60* (2018.01); *G16H 50/70* (2018.01);
(Continued)

(58) Field of Classification Search
CPC ........ G16H 20/17; G16H 20/60; G16H 20/70; G16H 20/90; G16H 50/20; G06F 19/3468;
(Continued)

(56) References Cited

U.S. PATENT DOCUMENTS 9,336,355 B2   5/2016   Ljuhs et al.
10,561,785 B2   2/2020   Roy et al.
(Continued)

FOREIGN PATENT DOCUMENTS

CA   2961887 A1 * 3/2016   ............ A61B 5/4839
EP   3892197 A1 * 10/2021   ............ A61B 5/0002
(Continued)

OTHER PUBLICATIONS

Finch, Tony, "Incremental calculation of weighted mean and variance", (2009), University of Cambridge Computing Service, all pages. https://fanf2.user.srcf.net/hermes/doc/antiforgery/stats.pdf (Year: 2009).*

(Continued)

*Primary Examiner* — Jason S Tiedeman
*Assistant Examiner* — Jessica Marie Webb
(74) *Attorney, Agent, or Firm* — Wesley Nicolas

(57) ABSTRACT

Systems and methods are provided for adjusting a basal/bolus ratio in a standing insulin regimen for a subject that comprises daily amounts of basal and bolus insulin medicaments that define an initial basal/bolus ratio. A data set comprising glucose measurements of the subject with a respective timestamp for each such measurement over a time course is obtained. One or more fasting events are identified in the time course. A temporal glucose gradient is computed for each fasting event using the glucose measurements in the data set within the fasting event time period. Fasting event glucose gradients are used to determine whether to recom- (Continued)

mend adjustment to the basal/bolus ratio for the subject without change to the daily total insulin medicament. The recommended adjustment to the basal/bolus ratio is communicated when the determination is made to make the recommended adjustment to the basal/bolus ratio for the subject.

28 Claims, 13 Drawing Sheets

(51) Int. Cl.
*G16H 10/60* (2018.01)
*G16H 80/00* (2018.01)
*A61M 5/172* (2006.01)
*A61B 5/145* (2006.01)
*A61B 5/00* (2006.01)

(52) U.S. Cl.
CPC ........ *A61B 5/14532* (2013.01); *A61M 5/1723* (2013.01); *G16H 80/00* (2018.01)

(58) Field of Classification Search
CPC .......... G06F 19/30; G06F 19/32; G06F 19/34; A61M 5/14; A61M 5/1723; G06Q 50/20–26
USPC ....................................................... 705/2, 3
See application file for complete search history.

(56) References Cited

U.S. PATENT DOCUMENTS

| | | | |
|---|---|---|---|
| 2008/0215367 A1* | 9/2008 | Marshall | G16H 50/70 705/3 |
| 2008/0234943 A1 | 9/2008 | Ray et al. | |
| 2009/0036753 A1 | 2/2009 | King | |
| 2009/0281519 A1 | 11/2009 | Rao et al. | |
| 2010/0185142 A1 | 7/2010 | Kamen et al. | |
| 2011/0275986 A1* | 11/2011 | Bashan | A61M 5/1684 604/66 |
| 2011/0313395 A1* | 12/2011 | Krulevitch | A61M 5/3129 604/504 |
| 2011/0319322 A1* | 12/2011 | Bashan | G16H 20/17 514/5.9 |
| 2012/0232520 A1* | 9/2012 | Sloan | G16Z 99/00 604/504 |
| 2012/0246106 A1* | 9/2012 | Atlas | A61B 5/14532 706/52 |
| 2013/0030358 A1* | 1/2013 | Yodfat | A61M 5/1413 604/66 |
| 2014/0019396 A1* | 1/2014 | Carlsgaard | G06N 5/02 706/46 |
| 2014/0313052 A1* | 10/2014 | Yarger | G16H 15/00 340/870.02 |
| 2014/0343530 A1* | 11/2014 | Bashan | G16H 10/40 604/504 |
| 2015/0217054 A1* | 8/2015 | Booth | G16H 80/00 604/504 |
| 2015/0217055 A1* | 8/2015 | Booth | A61P 3/10 604/504 |
| 2015/0366945 A1* | 12/2015 | Greene | A61M 5/1407 514/5.9 |
| 2016/0117481 A1* | 4/2016 | Booth | G16H 50/20 604/502 |
| 2016/0331285 A1* | 11/2016 | Choi | A61B 5/14514 |

FOREIGN PATENT DOCUMENTS

| | | | |
|---|---|---|---|
| JP | 2009037588 | A | 2/2009 |
| JP | 2013501989 | A | 1/2013 |
| JP | 2013529500 | A | 7/2013 |
| JP | 2015528348 | A | 9/2015 |
| WO | 07051139 | A2 | 5/2007 |
| WO | 2014035672 | A2 | 3/2014 |
| WO | 2015169814 | A1 | 11/2015 |
| WO | 2016069475 | A1 | 5/2016 |

OTHER PUBLICATIONS (N.a.), "Moving variance—MATLAB mowar", Jul. 21, 2016, MathWorks, all pages. http://web.archive.org/web/20160721045020/https://www.mathworks.com/help/matlab/ref/movvar.html (Year: 2016).*

(N.a.) Highlights of Prescribing Information: Novolog(R), Feb. 2015, U.S. Food and Drug Administration, all pages, https://www.accessdata.fda.gov/drugsatfda_docs/label/2015/020986s082lbl.pdf (Year: 2015).*

Eastman, Richard C., MD et al. "Rates of Glucose Change Measured by Blood Glucose Meter and the GlucoWatch Biographer During Day, Night, and Around Mealtimes", Sep. 2004, Diabetes Care, 27(9): 2161-2165, all pages. https://doi.org/10.2337/diacare.27.9.2161 . (Year: 2004).*

(N.a.) "Moving Average", Jun. 2016, and "Variance", Apr. 2016, From Wikipedia, Accessed through Wayback Machine, files combined in Adobe Acrobat, see all pages. (Year: 2016).*

Anonymous: "Insulin pen", Wikipedia, Oct. 22, 2015 (Oct. 22, 2015), XP055345788, Retrieved from the Internet: URL; https://en.wikipedia.org/w/index.php?tit(e=Insulin_pen&o(did=686984270, retrieved on Mar. 7, 2017.

Walsh et al., "Guidelines for Optimal Bolus Calculator Settings in Adults Author Affiliations", Journal of Diabetes Science and Technology, 2011, vol. 5, No. 1, pp. 129-135.

* cited by examiner

```
                                                                    ┌─ 402
┌──────────────────────────────────────────────────────────────┐
│ A device 250 for adjusting a basal/bolus ratio in a standing regimen for a subject is │
│ provided. The device comprises one or more processors 274 and a memory 290/ │
│ 192. The memory stores instructions that, when executed by the one or more │
│ processors, perform a method.                                │
└──────────────────────────────────────────────────────────────┘
                              │
                              ▼                          ┌─ 404
┌──────────────────────────────────────────────────────────────┐
│ Obtain a standing insulin regimen 206 for the subject. The standing insulin │
│ regimen for the subject comprises a daily total insulin medicament. The daily total │
│ insulin medicament is satisfied by a combination of a daily amount of a basal │
│ insulin medicament 210 and a daily amount of a bolus insulin medicament 214 │
│ specified by the standing insulin regimen for the subject. The daily amount of │
│ basal insulin medicament and the daily amount of bolus insulin medicament defines │
│ an initial basal/bolus ratio between the daily amount of basal insulin medicament │─ 406
│ and the daily amount of bolus insulin medicament.            │
│   ┌─ ─ ─ ─ ─ ─ ─ ─ ─ ─ ─ ─ ─ ─ ─ ─ ─ ─ ─ ─ ─ ─ ─ ─ ─ ─ ─ ─┐  │
│   │ The basal insulin medicament consists of a single insulin medicament │  │
│   │ having a duration of action that is between 12 and 24 hours or a mixture │  │
│   │ of insulin medicaments that collectively have a duration of action that is │  │
│   │ between 12 and 24 hours. The bolus insulin medicament consists of a │  │
│   │ single insulin medicament having a duration of action that is between │  │
│   │ three to eight hours or a mixture of insulin medicaments that │  │
│   │ collectively have a duration of action that is between three to eight │  │
│   │ hours.                                                   │  │
│   └─ ─ ─ ─ ─ ─ ─ ─ ─ ─ ─ ─ ─ ─ ─ ─ ─ ─ ─ ─ ─ ─ ─ ─ ─ ─ ─ ─┘  │
└──────────────────────────────────────────────────────────────┘
                              │                          ┌─ 408
                              ▼
┌──────────────────────────────────────────────────────────────┐
│ Obtain a first data set 216 comprising a plurality of glucose measurements of the │
│ subject taken over a time course and, for each respective glucose measurement 218 │
│ in the plurality of glucose measurements, a corresponding timestamp 220 │
│ representing when in the time course the respective glucose measurement was │─ 410
│ made.                                                        │
│   ┌─ ─ ─ ─ ─ ─ ─ ─ ─ ─ ─ ─ ─ ─ ─ ─ ─ ─ ─ ─ ─ ─ ─ ─ ─ ─ ─ ─┐  │
│   │ The device further comprises a wireless receiver, and the first data set 216 │  │
│   │ is obtained wirelessly from a glucose sensor 102 affixed to the subject. │  │
│   └─ ─ ─ ─ ─ ─ ─ ─ ─ ─ ─ ─ ─ ─ ─ ─ ─ ─ ─ ─ ─ ─ ─ ─ ─ ─ ─ ─┘  │
└──────────────────────────────────────────────────────────────┘
                              │
                              ▼
                            ( A )
```

The one or more fasting events is a single fasting event. The using the gradient of each fasting event in the one or more fasting events to determine whether to make a recommended adjustment to the basal/bolus ratio for the subject without change to the daily total insulin medicament comprises: deeming the standing insulin regimen for the subject basal deficient when the gradient of the single fasting event is positive and exceeds a positive threshold, deeming the standing insulin regimen for the subject bolus deficient when the gradient of the single fasting event is negative and exceeds a negative threshold, and otherwise, deeming the standing insulin regimen for the subject basal/bolus ratio sufficient.

— 434

The standing insulin regimen specifies that the daily amount of bolus insulin medicament is divided between two or more daily bolus injection event types in the set of event types comprising "breakfast," "lunch," and "dinner." The determination is made to make the recommended adjustment to the basal/bolus ratio. The recommended adjustment to the basal/bolus ratio is a recommended increase in the daily amount of bolus insulin medicament in the standing insulin regimen for the subject. The method further comprises determining which bolus injection event type in the two or more daily bolus injection event types is to be altered to have an increased bolus insulin medicament amount by determining a respective minimum post-prandial glucose measurement value associated with each respective bolus injection of each bolus injection event type in the two or more bolus injection events types across the time course. Then there is computed, for each respective daily bolus injection event type in the two or more daily bolus injection event types, a respective second measure of central tendency of the minimum post-prandial glucose measurement value associated with each respective bolus injection of the respective daily bolus injection event type thereby computing a plurality of second measures of central tendency. Further, there is selected, for the increased bolus insulin medicament amount, the daily bolus injection event type in the two or more daily bolus injection event types associated with the highest second measure of central tendency when the second measure of central tendency is more than a threshold amount higher than a third measure of central tendency of the plurality of second measures of central tendency. Otherwise, the increase in the bolus insulin medicament amount is distributed across the two or more daily bolus injection event types.

○ D    Fig. 4D

SYSTEMS AND METHODS FOR ADJUSTING A BASAL/BOLUS RATIO IN AN INSULIN REGIMEN

CROSS-REFERENCE TO RELATED APPLICATIONS

This application is a 35 U.S.C. § 371 National Stage application of International Application PCT/EP2017/070585 (published as WO 2018/033514), filed Aug. 14, 2017, which claims priority to European Patent Application 16184451.9, filed Aug. 17, 2016, the contents of all above-named applications are incorporated herein by reference.

TECHNICAL FIELD

The present disclosure relates generally to systems and methods for adjusting a basal/bolus ratio in a standing insulin regimen for a subject that comprises daily amounts of basal and bolus insulin medicaments that define an initial basal/bolus ratio in order to optimize the efficacy of the standing insulin regimen.

BACKGROUND

Type 2 diabetes mellitus is characterized by progressive disruption of normal physiologic insulin secretion. In healthy individuals, basal insulin secretion by pancreatic β cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, subjects with Type 2 diabetes are provided with insulin medicament treatment regimens. Subjects with Type 1 diabetes are also provided with insulin medicament treatment regimens. The goal of these insulin medicament treatment regimens is to maintain a desired fasting blood glucose target level that will minimize estimated risk of hypo- and hyper-glycaemia.

Traditional insulin medicament delivery systems have included the use of pump systems that provide a frequent recurrent dosage of insulin medicament. More recently, additional types of delivery systems have been developed, such as insulin pens, which can be used to self-administer insulin medicament treatment regimens in the form of less frequent insulin medicament injections. A common approach to diabetes treatment using such delivery systems is to inject a single short acting insulin medicament (bolus) dosage in accordance with a standing insulin regimen for the subject in response to or in anticipation of a meal event using one insulin pen. In such approaches, the subject injects the short acting insulin medicament dosage shortly before or after one or more meals each day to lower glucose levels resulting from such meals. Further, the subject injects a long acting insulin medicament (basal) dosage in accordance with the standing insulin regimen, independent of meal events, to maintain glycaemic control independent of meal events.

Thus, in traditional type 2 diabetes insulin treatment where both basal and bolus insulin medicament dosages are taken as described above, the ratio between basal and bolus insulin medicaments in the standing insulin medicament regimen is important in order to optimize glycaemic control. An optimal situation is for the bolus injections to account only for glucose from meals, and for the basal injections to lower baseline blood glucose and keep fasting blood glucose stable at the optimal blood glucose target levels. If this balance is disrupted, for example if too little basal insulin medicament is taken, the large bolus injections have to compensate for high baseline blood glucose causing unnecessary fluctuations in blood glucose levels, and blood glucose will typically rise during fasting periods.

In practice, the health care professional typically determines a total daily amount of insulin medicament the patient should take, counting both basal insulin medicament and bolus insulin medicament. The ratio between the two types of insulin medicament is then determined by "trial and error," starting at 50/50 (e.g. 30 units of fast acting insulin medicament and 30 units of slow acting insulin medicament, giving a total of 60 units) and is adjusted in follow up clinic visits until a desired blood glucose profile is reached. However, such approaches to ratio balancing are unsatisfactory because clinic visits happen fairly infrequently and thus it can take a long time to optimize the basil/bolus ratio in such approaches.

United States Patent Publication No. 20090281519 entitled "Automated System and Method for Diabetes Control" to the United States Veteran Affairs Department discloses an automated method and system of diabetes control. However, the methods disclosed in the 20090281519 publication are typically used in the intensive care unit (ICU) setting and require input data that is not readily available outside of such a setting. Moreover, at least one of the insulin medicaments administered, using the 20090281519 teaching, is administered intravenously on a drip line. As such, the publication does not offer satisfactory teachings on determining and communicating to a subject an optimal basal/bolus insulin medicament ratio for administrating insulin medicaments using insulin pens.

International Patent Publication WO2007/051139 entitled "Diabetes Management Systems and Methods" to Insulet Corporation discloses systems and methods for managing diabetes that makes use of substantially continuous glucose measurements from a subject. However, the WO2007/051139 publication relies upon the administration of insulin medicaments using a pump, and furthermore, does not seek to find an optimum basal/bolus ratio. Thus, like the 20090281519 publication, the WO2007/051139 publication does not offer satisfactory teachings on determining and communicating to a subject an optimal basal/bolus insulin medicament ratio for administrating insulin medicaments using insulin pens.

United States Patent Publication No. 20090036753 entitled "Continuous Glucose Monitoring-Directed Adjustments in Basal Insulin Rate and Insulin Bolus Dosing Formulas" to Diabetes Care Center discloses a therapeutic method for the management of diabetes care in insulin-dependent subjects that monitors glucose levels continuously and makes insulin-dose adjustments accordingly. Embodiments of the invention provide for the logging and analytical evaluation of daily continuous glucose monitoring (CGM) data, and for the generation of continuous glucose-driven-insulin adjustments (CGIA) that are delivered to the patient's insulin pump to achieve control glucose to a near normal level, without causing hypoglycemia. With reference to FIG. 8, showing the glucose level as a function of time, it appears that the patient's basal level of glucose is too high. The disclosed analysis begins with the question: "is there a glucose pattern?" A review of the data would note that the pattern is repeated for two days. The elevated glucose depicted in FIG. 8 could be due to an inadequate meal insulin bolus or due to an inadequate insulin basal rate. Omitting this meal will allow the isolated evaluation of an inadequate insulin basal rate. The patient's diary notes should be checked for any other event that may have taken place during this time. In FIG. 8, the pattern shows glucose elevated to a peak level of 200 mg/dL during the time period 2300 to 0500 hours. The basal insulin infusion rate can then be corrected according to a formula for changing the basal rate, and thereby also changing the daily total insulin.

Thus, like the 20090281519 publication, and the WO2007/051139 publication, the 20090036753 does not offer satisfactory teachings on determining and communicating to a subject an optimal basal/bolus insulin medicament ratio for administrating insulin medicaments using insulin pens. Given the above background, what is needed in the art are systems and methods for determining and communicating to a subject an optimal basal/bolus insulin medicament ratio for administration of insulin medicaments with insulin pens in order to minimize glycaemic risk.

SUMMARY

The present disclosure addresses the need in the art for systems and methods for adjusting a basal/bolus ratio in a standing insulin regimen for a subject. In the present disclosure, the subject has an initial standing insulin regimen that comprises daily amounts of basal and bolus insulin medicaments that define an initial basal/bolus ratio. A first data set comprising glucose measurements of the subject is obtained with a respective timestamp for each such measurement over a time course. One or more fasting events are identified in the time course. A temporal glucose gradient is computed for each fasting event using the glucose measurements in the first data set within the fasting event time period. Fasting event glucose gradients are used to determine whether to recommend adjustment to the basal/bolus ratio for the subject without change to the daily total insulin medicament. The recommended adjustment to the basal/bolus ratio is communicated when the determination is made to make the recommended adjustment to the basal/bolus ratio for the subject.

As such, one aspect of the present disclosure provides a device for adjusting a basal/bolus ratio in a standing insulin regimen for a subject. The device comprises one or more processors and a memory. The memory stores instructions that, when executed by the one or more processors, perform a method of obtaining the standing insulin regimen for the subject. The standing insulin regimen for the subject comprises a daily total insulin medicament. The daily total insulin medicament is satisfied by a combination of a daily amount of a basal insulin medicament and a daily amount of a bolus insulin medicament specified by the standing insulin regimen for the subject. The daily amount of basal insulin medicament and the daily amount of bolus insulin medicament defines an initial basal/bolus ratio between the daily amount of basal insulin medicament and the daily amount of bolus insulin medicament. A first data set is obtained. The first data set comprises a plurality of glucose measurements of the subject over a time course, and, for each respective glucose measurement in the plurality of glucose measurements, a timestamp representing when the respective measurement was made. One or more fasting events in the time course are identified. A respective temporal glucose gradient is computed, for each respective fasting event in the one or more fasting events, using the glucose measurements of the subject obtained from the first data set that are in a time period of the respective fasting event. The gradient of each fasting event in the one or more fasting events is used to determine whether to make a recommended adjustment to the basal/bolus ratio for the subject without change to the daily total insulin medicament. The recommended adjustment to the basal/bolus ratio is communicated, when the determination is made to make the recommended adjustment to the basal/bolus ratio for the subject, to: (i) the subject for manual adjustment of the basal/bolus ratio in the standing insulin regimen, (ii) each insulin pen in one or more insulin pens charged with delivering the standing insulin regimen to the subject, as dosage adjustment instructions, or (iii) a health care practitioner associated with the subject.

The temporal glucose gradient can be computed by any method of numerical differentiation. For example a line can be numerically fitted to a data set of glucose measurements comprising time stamps and corresponding glucose measurement values. The gradient can be evaluated as the slope of the fitted line by evaluating the difference between the glucose values on the line over the difference between corresponding time values. The recommended adjustment, can be an increase or a decrease in the ratio which will tend to minimize the gradient. The process of bringing the gradient to a minimum can be iterative.

In a further aspect, the standing insulin regimen for the subject further comprises a post-prandial glucose target, and an amount of correction bolus insulin medicament to account for a post-prandial glucose level above the post-prandial glucose target, wherein the correction bolus is specified to be administered by the one or more insulin pens.

In this way the correction bolus insulin medicament accounts for a food related rise in blood glucose levels, if the subject ingests more food than accounted for by the daily amount of bolus medicament, which is a portion of daily total insulin medicament. In other words the amount of medicament originating from correction boluses is not included in the daily amount of bolus medicament, and is therefore not included in the calculation of the daily total insulin medicament. Correction bolus is a common component of an insulin regimen for so called replacement therapy, i.e., basal-bolus insulin and bolus correction to account for high blood glucose levels before and after meals.

In a further aspect, the standing insulin regimen for the subject further comprises a lower range glucose target, and a carbohydrate correction to account for a glucose level below the lower range glucose target, wherein the carbohydrate correction can be administered orally, which ensures that the subject can prevent a hypoglycemic event.

In some embodiments, the one or more fasting events is a plurality of fasting events, and the step of using the gradient of each fasting event in the one or more fasting events to determine whether to make a recommended adjustment to the basal/bolus ratio for the subject without change to the daily total insulin medicament comprises taking a first measure of central tendency of the gradient of each fasting event in the plurality of fasting events. In such embodiments the standing insulin regimen for the subject is deemed basal deficient when the first measure of central tendency is positive and exceeds a positive threshold. The standing insulin regimen for the subject is deemed bolus deficient when the first measure of central tendency is negative and exceeds a negative threshold. Otherwise, the standing insulin regimen for the subject basal/bolus ratio is deemed sufficient.

In some embodiments, the one or more fasting events is a single fasting event, and the steps of using the gradient of each fasting event in the one or more fasting events to determine whether to make a recommended adjustment to the basal/bolus ratio for the subject without change to the daily total insulin medicament comprises: deeming the standing insulin regimen for the subject basal deficient when the gradient of the single fasting event is positive and exceeds a positive threshold, deeming the standing insulin regimen for the subject bolus deficient when the gradient of the single fasting event is negative and exceeds a negative threshold, and otherwise, deeming the standing insulin regimen for the subject basal/bolus ratio sufficient.

In some embodiments, each glucose measurements in the plurality of glucose measurements is autonomously measured and the one or more fasting events are determined using the plurality of glucose measurements of the subject and the respective timestamps in the first data set. In some such embodiments, the identifying the plurality of fasting events comprises identifying a first fasting period in a first time period encompassed by the time course by: computing a moving period of variance $\sigma_k^2$ across the plurality of glucose measurements using the expression $$\sigma_k^2 = \frac{1}{M} \sum_{i=k-M}^{k} (G_i - \overline{G})^2$$

where $G_i$ is the $i^{th}$ glucose measurement in a portion of the plurality of glucose measurements, M is a number of glucose measurements in the plurality of glucose measurements and represents a contiguous predetermined time span, $\overline{G}$ is the mean of the glucose measurements selected from the plurality of glucose measurements, and k is within the first time period. The first fasting period is then associated with a period of minimum variance $_k^{min}\sigma_k^2$ within the first time period.

In some embodiments, the identifying the one or more fasting events comprises receiving an indication of each fasting event in the one or more fasting events from the subject.

In some embodiments, the identifying the one or more fasting events comprises receiving a second data set from a wearable device worn by the subject. In such embodiments, the second data set indicates a physiological metric of the user during the time course that is indicative of the one or more fasting events.

In some embodiments, the standing insulin regimen specifies that the daily amount of bolus insulin medicament is divided between two or more daily bolus injection event types in the set of event types comprising "breakfast," "lunch," and "dinner." In some such embodiments, a determination is made to make the recommended adjustment to the basal/bolus ratio. This recommended adjustment to the basal/bolus ratio is a recommended increase in the daily amount of bolus insulin medicament in the standing insulin regimen for the subject and the method further comprises determining which bolus injection event type in the two or more daily bolus injection event types is to be altered to have an increased bolus insulin medicament amount. This is done by determining a respective minimum post-prandial glucose measurement value associated with each respective bolus injection of each bolus injection event type in the two or more bolus injection events types across the time course. For each respective daily bolus injection event type in the two or more daily bolus injection event types, a respective second measure of central tendency of the minimum post-prandial glucose measurement value associated with each respective bolus injection of the respective daily bolus injection event type is computed thereby computing a plurality of second measures of central tendency. Then, there is selected, for the increased bolus insulin medicament amount, the daily bolus injection event type in the two or more daily bolus injection event types associated with the highest second measure of central tendency when the second measure of central tendency is more than a threshold amount higher than a third measure of central tendency of the plurality of second measures of central tendency. Otherwise, this increase in the bolus insulin medicament amount is distributed across the two or more daily bolus injection event types.

In some embodiments, the standing insulin regimen specifies that the daily amount of bolus insulin medicament is divided between two or more daily bolus injection event types in the set of event types comprising "breakfast," "lunch," and "dinner" and a determination is made to make the recommended adjustment to the basal/bolus ratio. The recommended adjustment to the basal/bolus ratio is a recommended decrease in the daily amount of bolus insulin medicament in the standing insulin regimen for the subject. In such embodiments, the method further comprises determining which bolus injection event type in the two or more daily bolus injection event types is to be altered to have a decrease in bolus insulin medicament amount by determining a respective minimum post-prandial glucose measurement value associated with each respective bolus injection of each bolus injection event type in the two or more bolus injection events types across the time course. There is computed, for each respective daily bolus injection event type in the two or more daily bolus injection event types, a respective second measure of central tendency of the minimum post-prandial glucose measurement value associated with each respective bolus injection of the respective daily bolus injection event type thereby computing a plurality of second measures of central tendency. There is selected, for the decreased bolus insulin medicament amount, the daily bolus injection event type in the two or more daily bolus injection event types associated with the lowest second measure of central tendency when the second measure of central tendency is more than a threshold amount lower than a third measure of central tendency of the plurality of second measures of central tendency. Otherwise, the decrease in the bolus insulin medicament amount is distributed across the two or more daily bolus injection event types.

In some embodiments, a third data set is obtained from one or more insulin pens used by the subject to apply the standing insulin regimen. The third data set comprises a plurality of insulin medicament records. Each insulin medicament record in the plurality of medicament records comprises: (i) a respective insulin medicament injection event including an amount of insulin medicament injected into the subject using a respective insulin pen in the one or more insulin pens, (ii) a corresponding electronic timestamp that is automatically generated by the respective insulin pen upon occurrence of the respective insulin medicament injection event, and (iii) a respective type of insulin medicament injected into the subject from one of (a) the long acting insulin medicament and (b) the short acting insulin medicament. The third data set is used to exclude fasting events from the one or more fasting events that do not occur within a first predetermined time interval after a bolus injection event or within a second predetermined time interval after a basal injection event.

In some embodiments, the one or more fasting events are within the last week, within the last two weeks, or within the last month and wherein the method is repeated on a recurring basis over time.

In some embodiments, a determination is made to make the recommended adjustment to the basal/bolus ratio for the subject and wherein the adjustment is between 1 and 5 percent of the initial basal/bolus ratio, between 5 and 10 percent of the initial basal/bolus ratio, or between 10 and 15 percent of the initial basal/bolus ratio.

In some embodiments, the device further comprises a wireless receiver and wherein the first data set is obtained wirelessly from a glucose sensor affixed to the subject.

In some embodiments, the basal insulin medicament consists of a single insulin medicament having a duration of action that is between 12 and 24 hours or a mixture of insulin medicaments that collectively have a duration of action that is between 12 and 24 hours, and the bolus insulin medicament consists of a single insulin medicament having a duration of action that is between three to eight hours or a mixture of insulin medicaments that collectively have a duration of action that is between three to eight hours.

Another aspect of the present disclosure provides a method for adjusting a basal/bolus ratio in a standing insulin regimen for a subject. The method occurs at a computer system comprising one or more processors and a memory. In the method, the standing insulin regimen is obtained for the subject. The standing insulin regimen comprises a daily total insulin medicament. The daily total insulin medicament is satisfied by a combination of a daily amount of a basal insulin medicament and a daily amount of a bolus insulin medicament specified by the standing insulin regimen for the subject. The daily amount of basal insulin medicament and the daily amount of bolus insulin medicament defines an initial basal/bolus ratio between the daily amount of basal insulin medicament and the daily amount of bolus insulin medicament. In the method, a first data set is obtained. The first data set comprises a plurality of glucose measurements of the subject over a time course, and, for each respective glucose measurement in the plurality of glucose measurements, a timestamp representing when the respective measurement was made. One or more fasting events in the time course are identified. A respective temporal glucose gradient is computed, for each respective fasting event in the one or more fasting events, using the glucose measurements of the subject obtained from the first data set that are in a time period of the respective fasting event. The gradient of each fasting event in the one or more fasting events is used to determine whether to make a recommended adjustment to the basal/bolus ratio for the subject without change to the daily total insulin medicament. The recommended adjustment to the basal/bolus ratio is communicated, when the determination is made to make the recommended adjustment to the basal/bolus ratio for the subject, to: (i) the subject for manual adjustment of the basal/bolus ratio in the standing insulin regimen, (ii) each insulin pen in one or more insulin pens charged with delivering the standing insulin regimen to the subject, as dosage adjustment instructions, or (iii) a health care practitioner associated with the subject.

In a further aspect is provided, a computer program comprising instructions that, when executed by one or more processors, perform the method of:

obtaining the standing insulin regimen (206) for the subject, wherein the standing insulin regimen for the subject comprises a daily total insulin medicament, the daily total insulin medicament is satisfied by a combination of a daily amount of a basal insulin medicament (210) and a daily amount of a bolus insulin medicament (214) specified by the standing insulin regimen for the subject that is administered by one or more insulin pens, and the daily amount of basal insulin medicament and the daily amount of bolus insulin medicament defines an initial basal/bolus ratio between the daily amount of basal insulin medicament and the daily amount of bolus insulin medicament;

obtaining a first data set (216), the first data set comprising a plurality of glucose measurements of the subject over a time course, and, for each respective glucose measurement (218) in the plurality of glucose measurements, a timestamp (220) representing when the respective measurement was made;

identifying one or more fasting events in the time course;

computing a respective temporal glucose gradient (226), for each respective fasting event (224) in the one or more fasting events, using the glucose measurements of the subject obtained from the first data set that are in a time period (228) of the respective fasting event;

using the gradient of each fasting event in the one or more fasting events to determine whether to make a recommended adjustment to the basal/bolus ratio for the subject without change to the daily total insulin medicament; and communicating the recommended adjustment to the basal/bolus ratio, when the determination is made to make the recommended adjustment to the basal/bolus ratio for the subject, to:

(i) the subject for manual adjustment of the basal/bolus ratio in the standing insulin regimen, (ii) each insulin pen in the one or more insulin pens charged with delivering the standing insulin regimen to the subject, as dosage adjustment instructions, or (iii) a health care practitioner associated with the subject.

In a further aspect is provided, a computer-readable data carrier having stored thereon the computer program as defined above.

BRIEF DESCRIPTION OF THE DRAWINGS

FIGS. 4A, 4B, 4C, 4D, and 4E collectively provide a flow chart of processes and features of a device for adjusting a basal/bolus ratio in a standing insulin regimen for a subject, where optional elements of the flow chart are indicated by dashed boxes, in accordance with various embodiments of the present disclosure.

Like reference numerals refer to corresponding parts throughout the several views of the drawings.

DETAILED DESCRIPTION

Figure 1:
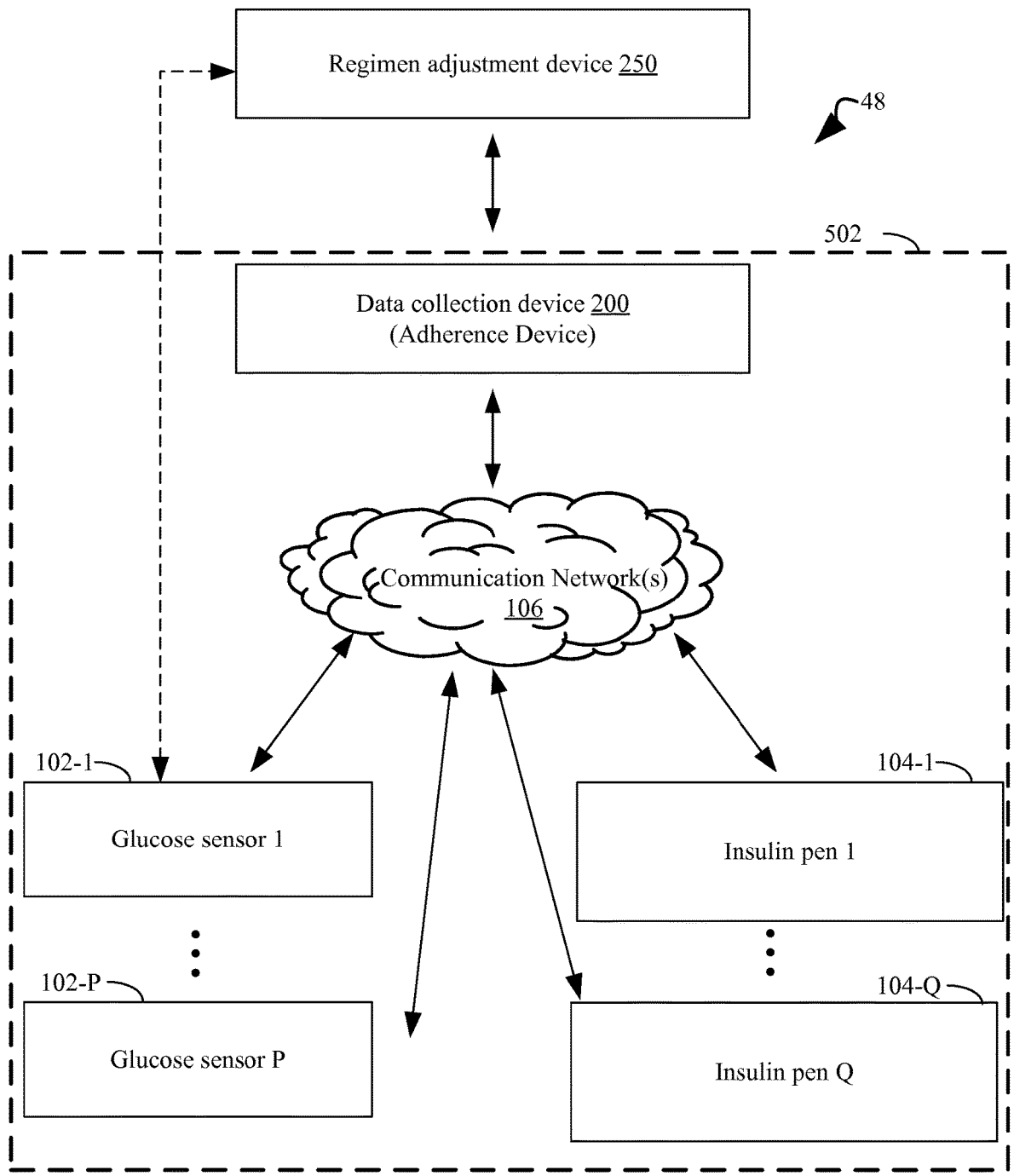
FIG. 1 illustrates an exemplary system topology that includes a regimen adjustment device for adjusting a basal/bolus ratio in a standing insulin regimen for a subject, a data collection device for collecting patient data, one or more glucose sensors that measure glucose data from the subject, and one or more insulin pens that are used by the subject to inject insulin medicaments in accordance with the prescribed insulin regimen, where the above-identified components are interconnected, optionally through a communications network, in accordance with an embodiment of the present disclosure.
Figure 5:
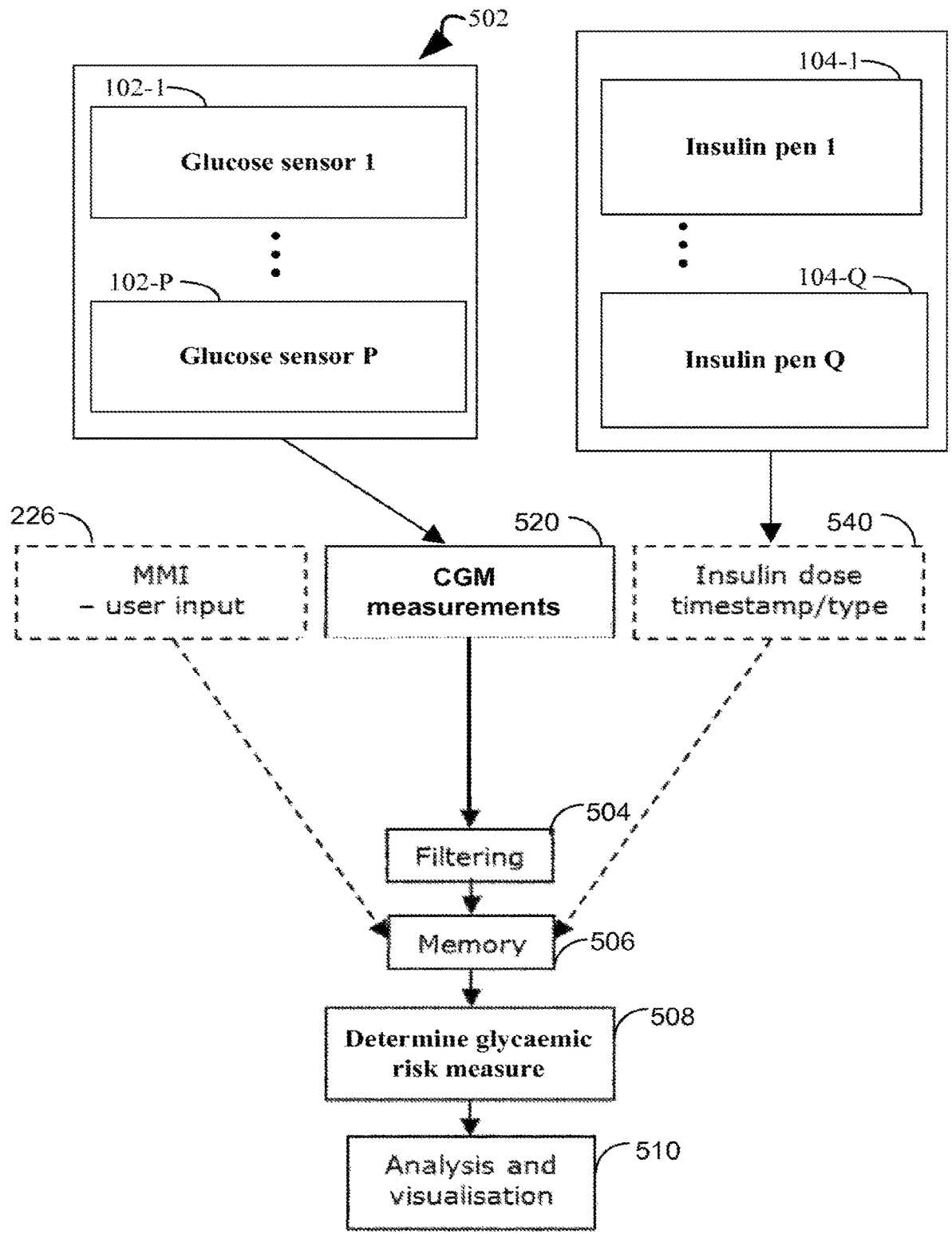
FIG. 5 illustrates an example integrated system of connected insulin pen(s), continuous glucose monitor(s), memory and a processor for adjusting a basal/bolus ratio in a standing insulin regimen for a subject in accordance with an embodiment of the present disclosure.

The present disclosure provides systems and methods for adjusting a basal/bolus ratio in a standing insulin regimen for a subject. FIG. 1 illustrates an example of an integrated system 502 for adjusting a basal/bolus ratio in a standing insulin regimen for a subject, and FIG. 5 provides more details of such a system 502. The integrated system 502 includes one or more connected insulin pens 104, one or more glucose monitors 102, memory 506, and a processor (not shown) for adjusting a basal/bolus ratio in a standing insulin regimen for a subject. In some embodiments, a glucose monitor 102 is a continuous glucose monitor.

With the integrated system, a basal/bolus ratio is adjusted for a standing insulin regimen for a subject, where the standing insulin regimen comprises daily amounts of basal insulin medicament and daily amounts of bolus insulin medicament that define an initial basal/bolus ratio. A data set comprising glucose measurements of the subject with a respective timestamp for each such measurement over a time course is obtained. One or more fasting events are identified in the time course. A temporal glucose gradient is computed for each fasting event using the glucose measurements in the first data set within the fasting event time period. Fasting event glucose gradients are used to determine whether to recommend adjustment to the basal/bolus ratio for the subject without change to the daily total insulin medicament. The recommended adjustment to the basal/bolus ratio is communicated when the determination is made to make the recommended adjustment to the basal/bolus ratio for the subject.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein. By the term insulin pen, is meant an injection device suitable for applying discrete doses of insulin, where the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2:
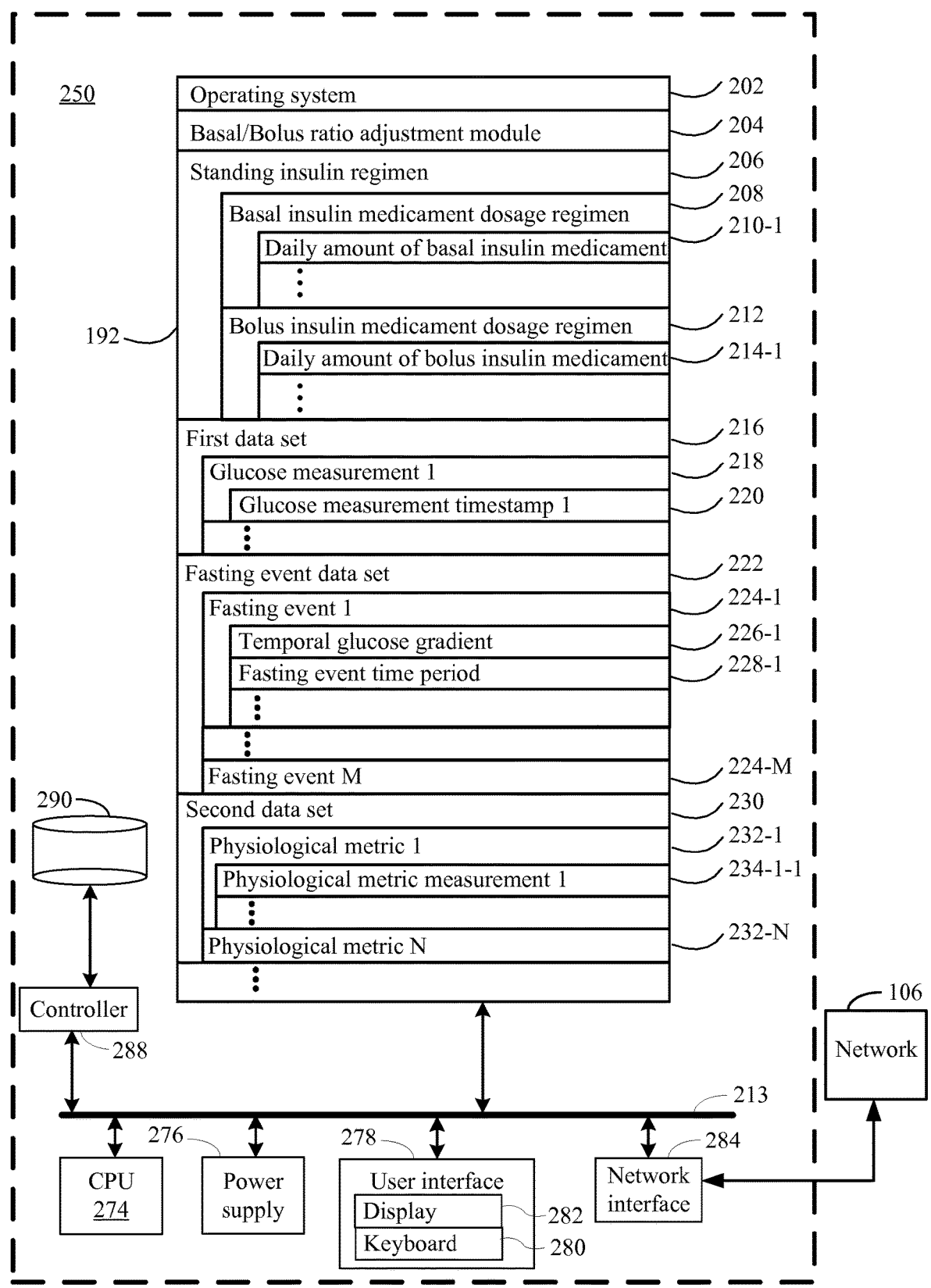
FIG. 2 illustrates a device for adjusting a basal/bolus ratio in a standing insulin regimen for a subject in accordance with an embodiment of the present disclosure.
Figure 3:
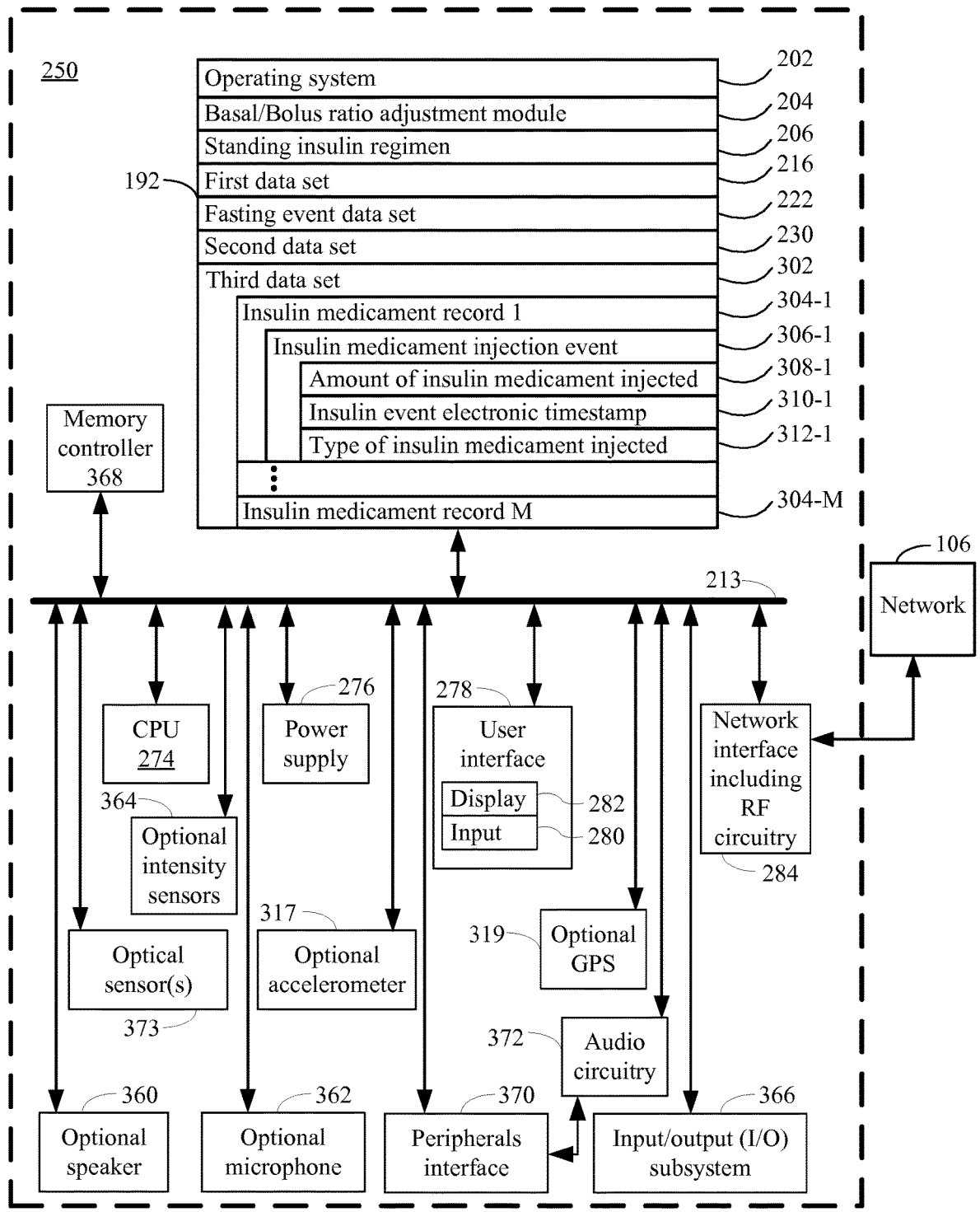
FIG. 3 illustrates a device for adjusting a basal/bolus ratio in a standing insulin regimen for a subject in accordance with another embodiment of the present disclosure.

A detailed description of a system 48 for adjusting a basal/bolus ratio in a standing insulin regimen for a subject in accordance with the present disclosure is described in conjunction with FIGS. 1 through 3. As such, FIGS. 1 through 3 collectively illustrate the topology of the system in accordance with the present disclosure. In the topology, there is a regimen adjustment device for adjusting a basal/bolus ratio in a standing insulin regimen for a subject ("regimen adjustment device 250") (FIGS. 1, 2, and 3), a device for data collection ("data collection device 200"), one or more glucose sensors 102 associated with the subject (FIGS. 1 and 5), and one or more insulin pens 104 for injecting insulin medicaments into the subject (FIGS. 1 and 5). Throughout the present disclosure, the data collection device 200 and the regimen adjustment device 250 will be referenced as separate devices solely for purposes of clarity. That is, the disclosed functionality of the data collection device 200 and the disclosed functionality of the regimen adjustment device 250 are contained in separate devices as illustrated in FIG. 1. However, it will be appreciated that, in fact, in some embodiments, the disclosed functionality of the data collection device 200 and the disclosed functionality of the regimen adjustment device 250 are contained in a single device. In some embodiments, the disclosed functionality of the data collection device 200 and/or the disclosed functionality of the regimen adjustment device 250 are contained in a single device and this single device is a glucose monitor 102 or an insulin pen 104.

Referring to FIG. 1, the regimen adjustment device 250 adjust a basal/bolus ratio in a standing insulin regimen for a subject. To do this, the data collection device 200, which is in electrical communication with the regimen adjustment device 250, receives glucose measurements originating from one or more glucose sensors 102 attached to a subject on an ongoing basis. In some embodiments, the data collection device 200 also receives insulin medicament injection data from one or more insulin pens 104 used by the subject to inject insulin medicaments. In some embodiments, the data collection device 200 receives such data directly from the glucose sensor(s) 102 and insulin pens 104 used by the subject. For instance, in some embodiments the data collection device 200 receives this data wirelessly through radio-frequency signals. In some embodiments such signals are in accordance with an 802.11 (WiFi), Bluetooth, or ZigBee standard. In some embodiments, the data collection device 200 receives such data directly, analyzes the data, and passes the analyzed data to the regimen adjustment device 250. In some embodiments, a glucose sensor 102 and/or insulin pen 104 includes an RFID tag and communicates to the data collection device 200 and/or the regimen adjustment device 250 using RFID communication. In some embodiments, referring to FIG. 2, the data collection device 200 also obtains or receives physiological measurements 234 of the subject (e.g., from wearable physiological measurement devices, from measurement devices within the data collection device 200 such as a magnetometer or a thermostat, etc.).

In some embodiments, the data collection device 200 and/or the regimen adjustment device 250 is not proximate to the subject and/or does not have wireless capabilities or such wireless capabilities are not used for the purpose of acquiring glucose data, insulin medicament injection data, and/or physiological measurement data. In such embodiments, a communication network 106 may be used to communicate glucose measurements from the glucose sensor 102 to the data collection device 200 and/or the regimen adjustment device 250, insulin medicament injection data from the one or more insulin pens 104 to the data collection device 200 and/or the regimen adjustment device 250, and/or physiological measurement data from one or more physiological measurement devices (not shown) to the data collection device 200 and/or the regimen adjustment device 250.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, there is a single glucose sensor 102 attached to the subject and the data collection device 200 and/or the regimen adjustment device 250 is part of the glucose sensor 102. That is, in some embodiments, the data collection device 200 and/or the regimen adjustment device 250 and the glucose sensor 102 are a single device.

In some embodiments, the data collection device 200 and/or the regimen adjustment device 250 is part of an insulin pen. That is, in some embodiments, the data collection device 200 and/or the regimen adjustment device 250 and an insulin pen 104 are a single device.

Of course, other topologies of the system 48 are possible. For instance, rather than relying on a communications network 106, the one or more glucose sensors 102 and the one or more insulin pens 104 may wirelessly transmit information directly to the data collection device 200 and/or regimen adjustment device 250. Further, the data collection device 200 and/or the regimen adjustment device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the regimen adjustment device 250 comprises one or more computers. For purposes of illustration in FIG. 2, the regimen adjustment device 250 is represented as a single computer that includes all of the functionality for adjusting a basal/bolus ratio in a standing insulin regimen for a subject. However, the disclosure is not so limited. In some embodiments, the functionality for adjusting a basal/bolus ratio in a standing insulin regimen for a subject is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary regimen adjustment device 250 for adjusting a basal/bolus ratio in a standing insulin regimen for a subject comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the regimen adjustment device 250 but that can be electronically accessed by the regimen adjustment device 250 over an Internet, intranet, or other form of network or electronic cable (illustrated as element 106 in FIG. 2) using network interface 284.

In some embodiments, the memory 192 of the regimen adjustment device 250 for adjusting a basal/bolus ratio in a standing insulin regimen for a subject stores:
- an operating system 202 that includes procedures for handling various basic system services;
- a basal/bolus ratio adjustment module 204;
- a standing insulin regimen 206 for the subject, the standing insulin regimen comprising a basal insulin medicament dosage regimen 208 with a daily amount of basal (long acting) insulin medicament 210 specified, and further comprising a bolus (short acting) insulin medicament dosage regimen 212 with a daily amount of bolus insulin medicament 214 specified;
- a first data set 216, the first data set representing a time course and comprising a plurality of glucose measurements of the subject over the time course, and for each respective glucose measurement 218 in the plurality of glucose measurements, a glucose measurement timestamp 220 representing when the respective glucose measurement was made;
- a fasting event data set 222 comprising a plurality of fasting events that occur in the time course encompassed by the first data set, each such fasting event 224 characterized by a temporal glucose gradient 226 and a corresponding fasting event time period 228 within the time course; and
- an optional second data set 230 that comprises one or more physiological metrics and, for each respective physiological metric 232 in the one or more physiological metrics, one or more physiological metric measurements 234 of the subject.

In some embodiments, the physiological metric measurement 234 is body temperature of the subject. In some embodiments, the physiological metric measurement 234 is a measurement of activity of the subject. In some embodiments, these physiological metric measurements serve as an additional input for identifying fasting events and/or for calculating a basal/bolus ratio. In some embodiments, the optional accelerometer 317, optional GPS 319, and/or magnetometer (not shown) of the regimen adjustment device 250 or such components optionally within the one or more glucose monitors 102 and/or the one or more insulin pens 104 is used to acquire such physiological metric measurements 234.

In some embodiments, the basal/bolus ratio adjustment module 204 is accessible within any browser (phone, tablet, laptop/desktop). In some embodiments, the basal/bolus ratio adjustment module 204 runs on native device frameworks, and is available for download onto the regimen adjustment device 250 running an operating system 202 such as Android or iOS.

In some implementations, one or more of the above identified data elements or modules of the regimen adjustment device 250 for adjusting a basal/bolus ratio in a standing insulin regimen for a subject are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments, the memory 192 and/or 290 stores additional modules and data structures not described above.

In some embodiments, a regimen adjustment device 250 for adjusting a basal/bolus ratio in a standing insulin regimen for a subject is a smart phone (e.g., an iPHONE), laptop, tablet computer, desktop computer, or other form of electronic device (e.g., a gaming console). In some embodiments, the regimen adjustment device 250 is not mobile. In some embodiments, the regimen adjustment device 250 is mobile.

FIG. 3 provides a further description of a specific embodiment of a regimen adjustment device 250 in accordance with the instant disclosure. The regimen adjustment device 250 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the regimen adjustment device 250 (e.g., a touch-sensitive surface such as a touch-sensitive display system 282 of the regimen adjustment device 250), an optional input/output (I/O) subsystem 366, one or more optional optical sensors 373, one or more communication busses 213 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The regimen adjustment device 250 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the regimen adjustment device 250 and/or for determining an amount of physical exertion by the subject.

It should be appreciated that the regimen adjustment device 250 illustrated in FIG. 3 is only one example of a multifunction device that may be used for adjusting a basal/bolus ratio in a standing insulin regimen for a subject, and that the regimen adjustment device 250 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the regimen adjustment device 250 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the regimen adjustment device 250, such as CPU(s) 274 is, optionally, controlled by the memory controller 368.

In some embodiments, the memory 192 of the regimen adjustment device 250 illustrated in FIG. 3 optionally includes a third data set 302 comprising a plurality of insulin medicament records over the time course. Each insulin medicament record 304 in the plurality of medicament records comprises: (i) a respective insulin medicament injection event 306 including an amount of insulin medicament injected 308 into the subject using a respective insulin pen 104 in the one or more insulin pens, (ii) a corresponding insulin event electronic timestamp 310 that is automatically generated by the respective insulin pen 104 upon occurrence of the respective insulin medicament injection event, and (iii) a respective type of insulin medicament 312 injected into the subject from one of (a) the basal insulin medicament and (b) the bolus insulin medicament.

The peripherals interface 370 can be used to couple input and output peripherals of the device to CPU(s) 274 and memory 192. The one or more processors 274 run or execute various software programs and/or sets of instructions stored in memory 192, such as the basal/bolus ratio adjustment module 204, to perform various functions for the regimen adjustment device 250 and to process data.

In some embodiments, the peripherals interface 370, CPU(s) 274, and memory controller 368 are, optionally, implemented on a single chip. In some other embodiments, they are implemented on separate chips.

RF (radio frequency) circuitry of network interface 284 receives and sends RF signals, also called electromagnetic signals. In some embodiments, the standing insulin regimen 206, the first data set 218, the second data set 224, the plurality of bins 232, the optional third data set 302, and/or the optional additional data set 310 is received using this RF circuitry from one or more devices such as a glucose sensor 102 associated with a subject, an insulin pen 104 associated with the subject and/or the data collection device 200. In some embodiments, the RF circuitry 108 converts electrical signals to/from electromagnetic signals and communicates with communications networks and other communications devices, glucose sensors 102, and insulin pens 104 and/or the data collection device 200 via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the adjustment timing device 250. The audio circuitry 372 receives audio data from the peripherals interface 370, converts the audio data to electrical signals, and transmits the electrical signals to the speaker 360. The speaker 360 converts the electrical signals to human-audible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 192 and/or the RF circuitry 284 by the peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the regimen adjustment device 250 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the regimen adjustment device 250, opposite the display 282 on the front of the regimen adjustment device 250, so that the input 280 is enabled for use as a viewfinder for still and/or video image acquisition. In some embodiments, another optical sensor 373 is located on the front of the regimen adjustment device 250 so that the subject's image is obtained (e.g., to verify the health or condition of the subject, to determine the physical activity level of the subject, to help diagnose a subject's condition remotely, or to acquire visual physiological measurements 312 of the subject, etc.).

As illustrated in FIG. 3, a regimen adjustment device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the regimen adjustment device 250 is a smart phone. In other embodiments, the regimen adjustment device 250 is not a smart phone but rather is a tablet computer, desktop computer, emergency vehicle computer, or other form or wired or wireless networked device. In some embodiments, the regimen adjustment device 250 has any or all of the circuitry, hardware components, and software components found in the regimen adjustment device 250 depicted in FIG. 2 or 3. In the interest of brevity and clarity, only a few of the possible components of the regimen adjustment device 250 are shown in order to better emphasize the additional software modules that are installed on the adjustment timing device 250.

While the system 48 disclosed in FIG. 1 can work standalone, in some embodiments it can also be linked with electronic medical records to exchange information in any way.

Now that details of a system 48 for adjusting a basal/bolus ratio in a standing insulin regimen for a subject have been disclosed, details regarding a flow chart of processes and features of the system, in accordance with an embodiment of the present disclosure, are disclosed with reference to FIGS. 4A through 4E. In some embodiments, such processes and features of the system are carried out by the basal/bolus ratio adjustment module 204 illustrated in FIGS. 2 and 3.

Block 402. With reference to block 402 of FIG. 4A, the goal of insulin therapy in subjects with either type 1 diabetes mellitus or type 2 diabetes mellitus is to match as closely as possible normal physiologic insulin secretion to control fasting and postprandial plasma glucose. As illustrated in FIG. 2, a regimen adjustment device 250 comprises one or more processors 274 and a memory 192/290. The memory stores instructions that, when executed by the one or more processors, perform a method.

Blocks 404-406. In the method, a standing insulin regimen 206 for the subject is obtained. The standing insulin regimen for the subject comprises a daily total insulin medicament. The daily total insulin medicament is satisfied by a combination of a daily amount of a basal insulin medicament 210 and a daily amount of a bolus insulin medicament 214 specified by the standing insulin regimen for the subject. The daily amount of basal insulin medicament and the daily amount of bolus insulin medicament defines an initial basal/bolus ratio between the daily amount of basal insulin medicament and the daily amount of bolus insulin medicament.

In some embodiments, the basal insulin medicament specified by the basal insulin medicament dosage regimen 208 consists of a single insulin medicament having a duration of action that is between 12 and 24 hours or a mixture of insulin medicaments that collectively have a duration of action that is between 12 and 24 hours. Examples of such basal insulin medicaments include, but are not limited to, Insulin Degludec (developed by NOVO NORDISK under the brand name Tresiba), NPH (Schmid, 2007, "New options in insulin therapy," J Pediatria (Rio J). 83(Suppl 5): S146-S155), Glargine (LANTUS, Mar. 2, 2007), Insulin Glargine [rDNA origin] injection (Dunn et al. 2003, "An Updated Review of its Use in the Management of Diabetes Mellitus" Drugs 63: p. 1743), and Determir (Plank et al., 2005, "A double-blind, randomized, dose-response study investigating the pharmacodynamic and pharmacokinetic properties of the long-acting insulin analog detemir," Diabetes Care 28:1107-1112).

In some embodiments, the bolus insulin medicament specified by the bolus insulin medicament dosage regimen 212 comprises a single insulin medicament having a duration of action that is between three to eight hours or a mixture of insulin medicaments that collectively have a duration of action that is between three to eight hours. Examples of such basal insulin medicaments include, but are not limited, to Lispro (HUMALOG, May 18, 2001, insulin lispro [rDNA origin] injection, Indianapolis, Ind.: Eli Lilly and Company), Aspart (NOVOLOG, July 2011), insulin aspart [rDNA origin] injection, Princeton, N.J., NOVO NORDISK Inc., July, 2011), and Glulisine (Helms Kelley, 2009, "Insulin glulisine: an evaluation of its pharmacodynamic properties and clinical application," Ann Pharmacother 43:658-668), and Regular (Gerich, 2002, "Novel insulins: expanding options in diabetes management," Am J Med. 113:308-316).

In some embodiments, the basal insulin medicament dosage regimen 208 specifies two or more doses, such as in instances where a daily basal dose has been split into two daily doses to optimize the treatment regimen. In some embodiments, the bolus insulin medicament dosage regimen 212 specifies a first bolus insulin medicament dosage for breakfast and a second bolus insulin medicament dosage for lunch. In some embodiments, the bolus insulin medicament dosage regimen 212 specifies a first bolus insulin medicament dosage for breakfast, a second bolus insulin medicament dosage for lunch, and a third bolus insulin medicament dosage for dinner. In some embodiments, the bolus insulin medicament dosage regimen 212 specifies a first bolus insulin medicament dosage for a prospective meal event as a function of a number of carbohydrates the subject estimates will be in the prospective meal event. In some embodiments, the bolus insulin medicament dosage regimen 212 specifies a bolus insulin medicament dosage for a prospective meal event as a function of a number of carbohydrates the subject has historically consumed for the prospective meal event in the past. In some such embodiments, the bolus insulin medicament dosage regimen 212 specifies such bolus insulin medicament dosages for prospective meal events while preserving the daily basal/bolus insulin ratio of the standing insulin regime 206.

Blocks 408-410. Referring to block 408 of FIG. 4A, in the method, a first data set 216 is obtained. The first data set 216 comprises a plurality of glucose measurements of the subject taken over a time course. In typical embodiments, the glucose measurements are from one or more glucose sensors 102. FIG. 2 illustrates. Each such glucose measurement 218 is timestamped with a glucose measurement timestamp 220 to represent when the respective measurement was made. Thus, in some embodiments, the glucose measurements are measured without human intervention. That is, the subject does not manually make the glucose measurements. In alternative embodiments of the present disclosure, the subject or a health care practitioner manually takes glucose measurements and such manual glucose measurements are used as the glucose measurements 218 in the first data set 216.

In embodiments where autonomous glucose measurements are used in the first data set 216, devices such as the FREESTYLE LIBRE CGM by ABBOTT ("LIBRE") may serve as the glucose sensor 102 in order to make the plurality of autonomous glucose measurements of a subject. The LIBRE allows calibration-free glucose measurements with an on-skin coin-sized sensor, which can send up to eight hours of data to a reader device (e.g., the data collection device 200 and/or the regimen adjustment device 250) via near field communications, when brought close together. The LIBRE can be worn for fourteen days in all daily life activities. In some embodiments, the glucose measurements 218 are autonomously taken from the subject at an interval rate of 5 minutes or less, 3 minutes or less, or 1 minute or less. In some embodiments, the glucose measurements 218 are taken from the subject at an interval rate of 5 minutes or less, 3 minutes or less, or 1 minute or less, over a time period of a day or more, two days or more, a week or more, or two weeks or more. In some embodiments, the glucose measurements 218 are autonomously taken (e.g., without human effort, without human intervention, etc.). Referring to block 410 of FIG. 4A, in some embodiments the regimen adjustment device 250 further comprises a wireless receiver and the first data set 216 is obtained wirelessly from a glucose sensor 102 affixed to the subject (e.g., in accordance with an 802.11, Bluetooth, or ZigBee standard).

Figure 6:
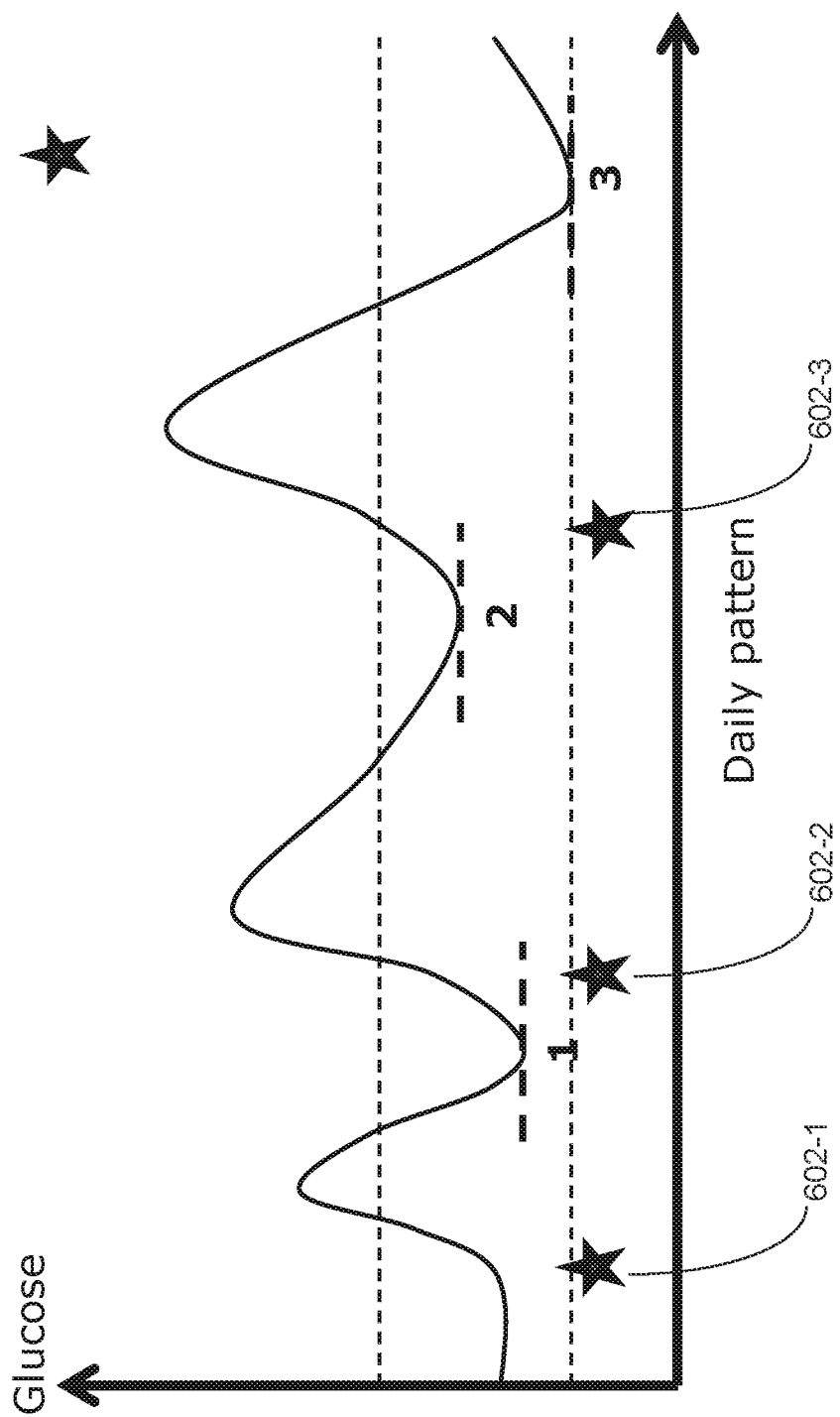
FIG. 6 illustrates the daily glucose pattern for subject in which meals are marked with stars, and in which bolus/basal ratio change is determined based on the lowest postprandial glucose values measured between the meals in accordance with an embodiment of the present disclosure.

Blocks 412-416. Referring to block 412 of FIG. 4B, the method continues by identifying one or more fasting events in the time course. FIG. 6 illustrates the daily glucose pattern for subject in which meals 602 are marked with stars, and in which bolus/basal ratio change is determined based on the lowest postprandial glucose values measured between the meals in accordance with an embodiment of the present disclosure. Referring to block 414, in some such embodiments, each glucose measurement 218 in the plurality of glucose measurements is autonomously measured and the fasting events 224 are determined using the plurality of glucose measurements of the subject and the respective timestamps in the first data set 216. In some such embodiments the fasting events are detected autonomously using a fasting detection algorithm and the glucose measurements in the first data set 216.

There are a number of methods for detecting a fasting event 224 using glucose measurements 218 from a glucose sensor 102. For instance, referring to block 416, in some embodiments a first fasting event 224 is identified in a first time period (e.g., a period of 24 hours) encompassed by the plurality of glucose measurements in the first data set 216 by first computing a moving period of variance $\sigma_k^2$ across the glucose measurements, where:

$$\sigma_k^2 = \frac{1}{M} \sum_{i=k-M}^{k} (G_i - \overline{G})^2$$

and where, $G_i$ is the $i^{th}$ glucose measurement in the portion of the plurality of glucose measurements considered, M is a number of glucose measurements in the plurality of glucose measurements and represents a contiguous predetermined time span, $\overline{G}$ is the mean of the M glucose measurements selected from the plurality of glucose measurements of the first data set 228, and k is within the first time period. As an example, the glucose measurements may span several days or weeks, with glucose measurements taken every five minutes. A first time period k (e.g., one day) within this overall time span is selected and thus the portion k of the plurality of measurements is examined for a period of minimum variance. The first fasting period is deemed to be the period of minimum variance $_k^{min}\sigma_k^2$ within the first time period. Next, the process is repeated with portion k of the plurality of glucose measurements by examining the next portion k of the plurality of glucose measurements for another period of minimum variance thereby assigning another fasting period.

Moreover, in some embodiments, only those fasting events that are deemed basal insulin medicament dosage regimen 208 adherent are used. Example 1, below, illustrates a way in which a determination is made as to whether a fasting event 224 is basal insulin medicament dosage regimen 208 adherent. Moreover, European Patent Application Number EP16177080.5, entitled "Regimen Adherence Measure for Insulin Treatment Base on Glucose Measurement and Insulin Pen Data," filed Jun. 30, 2016, which is hereby incorporated by reference, discloses techniques for identifying and classifying fasting events as adherent or nonadherent. In some embodiments, only those fasting events that are classified as "basal regimen adherent" in accordance with European Patent Application Number EP16177080.5 are used to adjust a basal/bolus ratio in a standing insulin regimen for a subject.

In typical embodiments, there is two or more than glucose measurements 218 for a given fasting event 224 encompassed by the first data set 230. In typical embodiments, there is three or more, four or more, five or more, six or more, seven or more, eight or more, nine or more, or ten or more glucose measurements 218 for a given fasting event 224 encompassed by the first data set 216. In some embodiments, the fasting event time period 228 for a given fasting event 224 specifies a time of day. In some embodiments, the fasting event time period 228 for a given fasting event 224 specifies a time span. In some embodiments, this time span is less than five minutes, less than 10 minutes, less than 20 minutes, or less than 30 minutes. In some embodiments this time span is between 5 minutes and 1 hour. In some embodiments this time span is between 30 minutes and 2 hours.

Block 418. Referring to block 418 of FIG. 4B, in some embodiments, the identifying the one or more of fasting events comprises receiving an indication of each fasting event 224 in the one or more fasting events from the subject in the form of feed-forward events. Each respective feed-forward event represents an instance where the subject has indicated they are fasting or are about to fast. In some embodiments, both an autonomous fast detection algorithm, such as one disclosed in block 416, and the manual (user indicated) fast detection are used for detecting fasting events 224. For instance, in some embodiments, a fasting event 224 that has been autonomously detected (e.g., using the algorithm of block 416) is then verified using the feed-forward events. To illustrate, when a fasting event 224 autonomously detected using an algorithm such as one disclosed in block 416 is matched in time (temporally matched) to a feed-forward event in which the subject indicated they are fasting, the fasting is deemed verified and used in further steps of the present disclosure.

In some embodiments, a fasting event 224 must be verified in this manner and also be deemed basal insulin medicament dosage regimen 208 adherent (e.g., deemed basal insulin medicament dosage regimen 208 adherent as disclosed in Example 1 below).

Block 420. Referring to block 420 of FIG. 4B, in some embodiments, the identifying the one or more fasting events comprises receiving a second data set 220 from a wearable device (e.g., from wearable physiological measurement devices, from measurement devices within the data collection device 200 such as a magnetometer or a thermostat, etc.), and the second data set indicates a physiological metric 232 of the user during the time course that is indicative of the one or more fasting events. In some embodiments, the physiological metric measurement 234 is body temperature of the subject. In some embodiments, the physiological metric measurement 234 is a measurement of activity of the subject. In some embodiments, the optional accelerometer 317, optional GPS 319, and/or magnetometer (not shown) of the regimen adjustment device 250 or such components optionally within the one or more glucose monitors 102 and/or the one or more insulin pens 104 is used to acquire such physiological metric measurements 234. In some embodiments, both an autonomous fast detection algorithm, such as one disclosed in block 416, and the physiological metric measurements are used for detecting fasting events 224. For instance, in some embodiments, a fasting event 224 is autonomously detected (e.g., by way of block 416) and verified using the physiological metric measurements 234.

To illustrate, when a fasting event autonomously detected using an algorithm such as one disclosed in block 416 is matched in time (temporally matched) to physiological metric measurements 234 which further indicate that the subject is fasting, the fasting is deemed verified and used in further steps of the present disclosure. In some embodiments, a fasting event 224 must be verified in this manner and also be deemed basal insulin medicament dosage regimen 208 adherent (e.g., deemed basal insulin medicament dosage regimen 208 adherent as disclosed in Example 1 below).

Block 422. Referring to block 422 of FIG. 4B, in some embodiments, the one or more fasting events are within the last week, within the last two weeks, or within the last month. In such embodiments, the method disclosed in FIGS. 4A through 4E is repeated over time so that the basal/bolus insulin ratio is updated on a recurring basis based upon updated glucose measurements.

Block 424. Embodiments in which the additional requirement that fasting events 224 be deemed basal insulin medicament dosage regimen 208 adherent in order to be used to optimize the basal/bolus ratio of the standing insulin regimen 206 have been described above. Referring to block 424 of FIG. 4C, in some embodiments, the fasting events 224 must be deemed both basal insulin medicament dosage regimen 208 adherent and bolus insulin medicament dosage regimen 212 adherent in order to be used to optimize the basal/bolus ratio of the standing insulin regimen. In one such embodiment, such fasting events are checked for basal and bolus regimen adherence by obtaining a third data set 302 from one or more insulin pens 104 used by the subject to apply the standing insulin regimen 206. The third data set 302 comprises a plurality of insulin medicament records. Each insulin medicament record 304 in the plurality of medicament records comprises: (i) a respective insulin medicament injection event 306 including an amount of insulin medicament injected 308 into the subject using a respective insulin pen in the one or more insulin pens, (ii) a corresponding insulin event electronic timestamp 310 that is automatically generated by the respective insulin pen upon occurrence of the respective insulin medicament injection event, and (iii) a respective type of insulin medicament injected 312 into the subject from one of (a) the basal insulin medicament and (b) the bolus insulin medicament. The third data set 302 is used to exclude fasting events from the one or more fasting events that do not occur within a first predetermined time interval after a bolus injection event or within a second predetermined time interval after a basal injection event. In some such embodiments, the first predetermined time interval is thirty minutes or less, one hour or less, four hours or less, or eight hours or less. In some such embodiments, the second predetermined time interval is different than the first predetermined time interval and is one hour or less, or four hours or less, eight hours or less, twelve hours or less, sixteen hours or less, twenty hours or less or twenty-four hours or less. In some embodiments, the first and second predetermined time interval is the same. In some embodiments, the fasting event time period 228 of each fasting event is compared to the insulin event electronic timestamps 310 in order to determine whether this requirement is satisfied.

Figure 7:
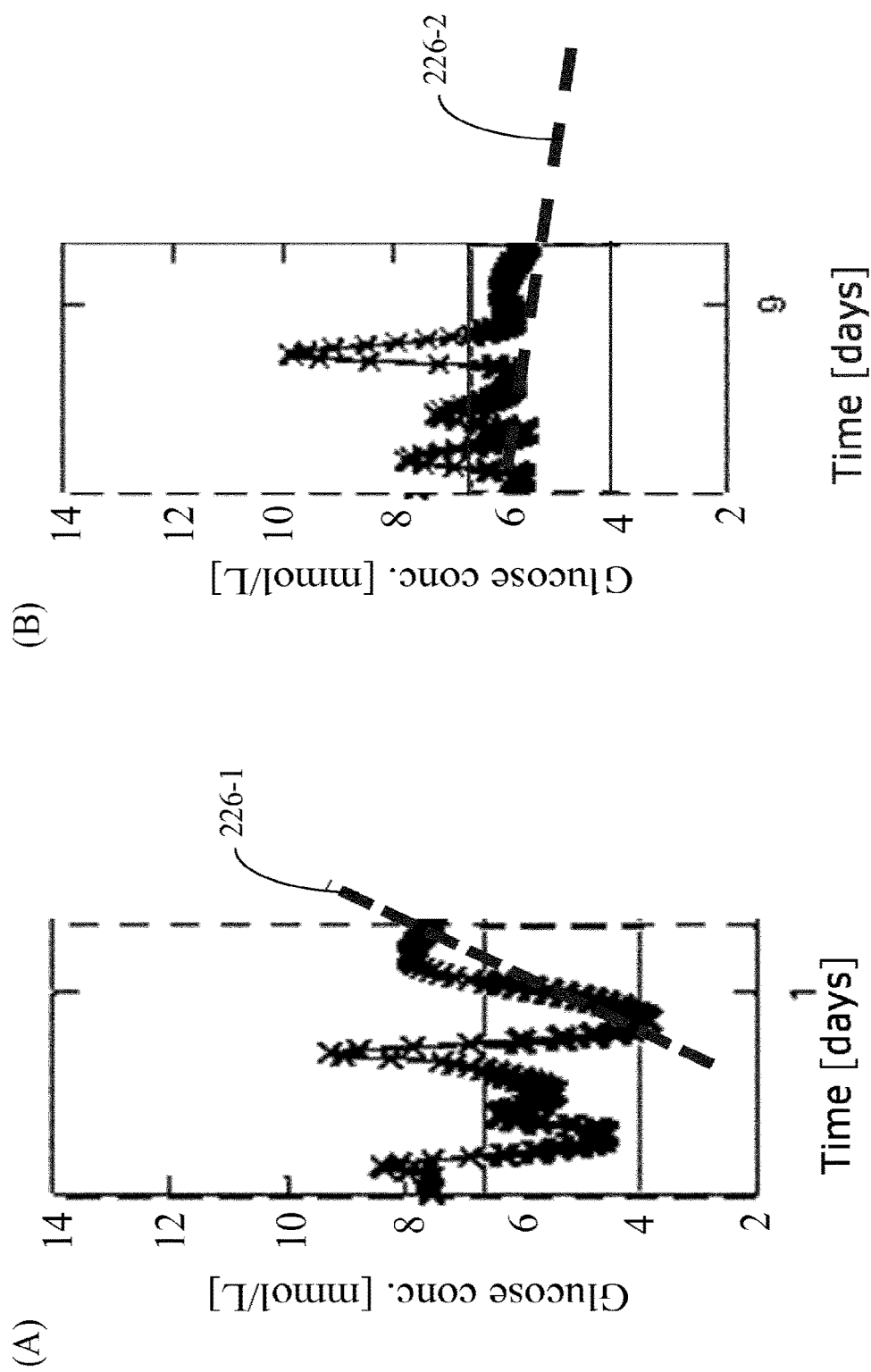
FIG. 7 illustrates temporal glucose gradients during fasting events in accordance with an embodiment of the present disclosure. In Panel A, the temporal glucose gradient is positive and larger than a defined tolerance, hence the basal is increased and the bolus decreased. In Panel B, the temporal glucose gradients is negative, but smaller than a defined tolerance, hence the basal and bolus ratio is held constant until the temporal glucose gradient indicates that a change should be made.

Block 426. Referring to block 426 of FIG. 4C, the method continues by computing a respective temporal glucose gradient 226, for each respective fasting event 224 in the one or more fasting events, using the glucose measurements of the subject obtained from the first data set that are in a time period 228 of the respective fasting event. FIG. 7 illustrates such temporal glucose gradients during fasting events in accordance with an embodiment of the present disclosure. In panel A of FIG. 7, the temporal glucose gradient 226-1 for a first fasting event 224-1 is positive and larger than a defined tolerance, hence the daily amount of basal insulin medicament 210 is increased relative to the daily amount of bolus insulin medicament 214. In Panel B, the temporal glucose gradient 226-2 for a second fasting event 224-2 is negative, but smaller than a defined tolerance, hence the basal/bolus ratio is held constant until the temporal glucose gradient 226 in a subsequent fasting event 224 indicates that a change should be made to the ratio.

As discussed above, in typical embodiments, there are several glucose measurements 218 in the fasting event time period 228 of any given fasting event 224. These glucose measurements are used to compute the temporal glucose gradient 226 of a given fasting event 224. In some embodiments, this is done using a linear method of regression such as least squares, least squares with subset selection (in which only some of the glucose measurements in a fasting period are used in accordance the subset selection techniques), or least squares with shrinkage (in which least square regression coefficients are minimized by imposing a penalty on their size). See Hastie, *The Elements of Statistical Learning, Data Mining, Inference, and Prediction*, Spinger-Verlag, 2003 Corrected Printing, Chapter 3, pp. 41-78, which is hereby incorporated by reference.

Block 428-432. Referring to block 428 of FIG. 4C, the method continues by using the temporal glucose gradient 226 of each fasting event 224 in the one or more fasting events to determine whether to make a recommended adjustment to the basal/bolus ratio for the subject without change to the daily total insulin medicament. That is, the total number of units of insulin medicament is kept the same but the amount of this total number that is prescribed as basal insulin medicament is changed relative to the amount of this total number that is prescribed as bolus insulin medicament. There are a number of ways this can be done and all such ways are encompassed within the present disclosure.

Figure 4B:
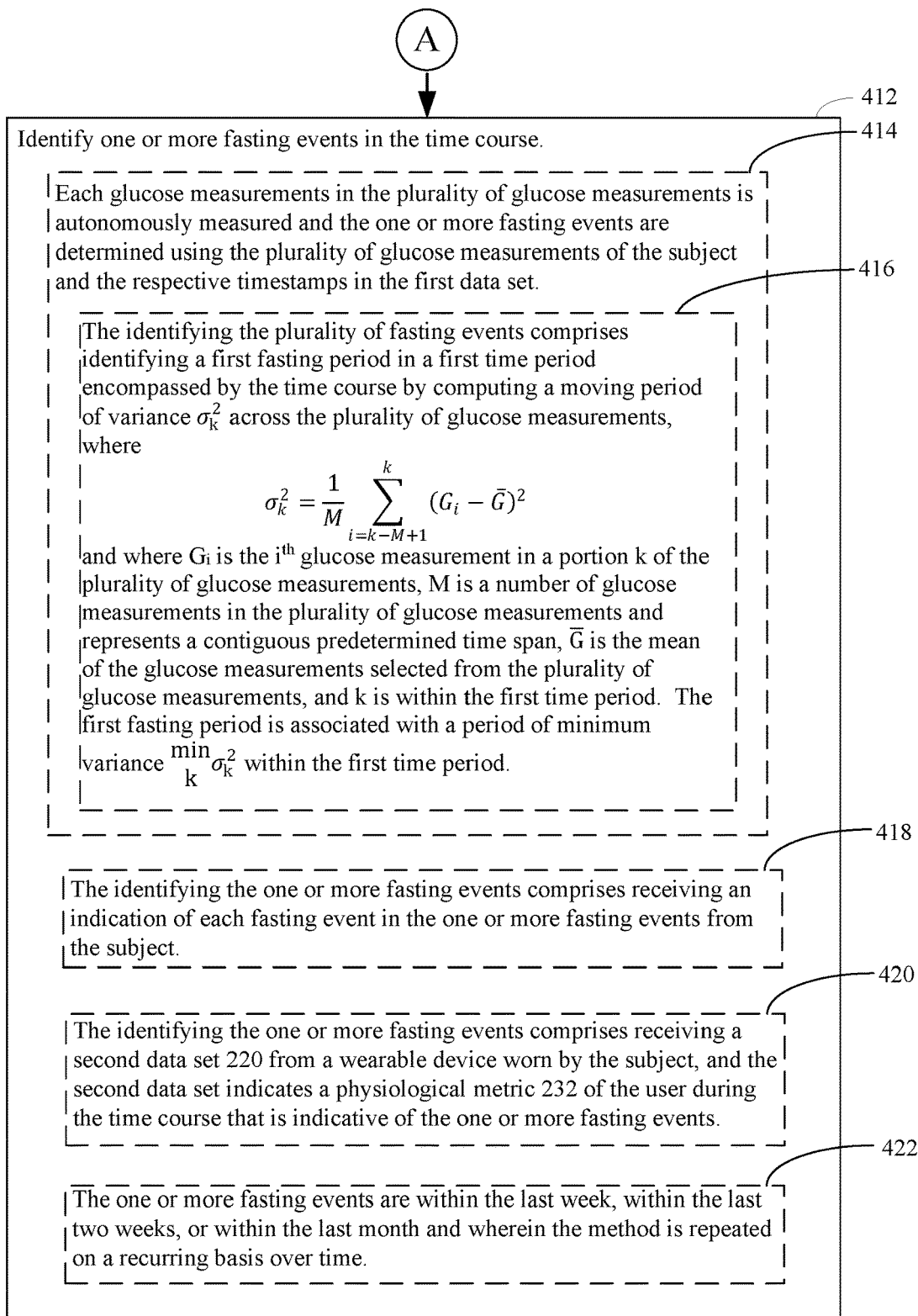
Figure 4C:
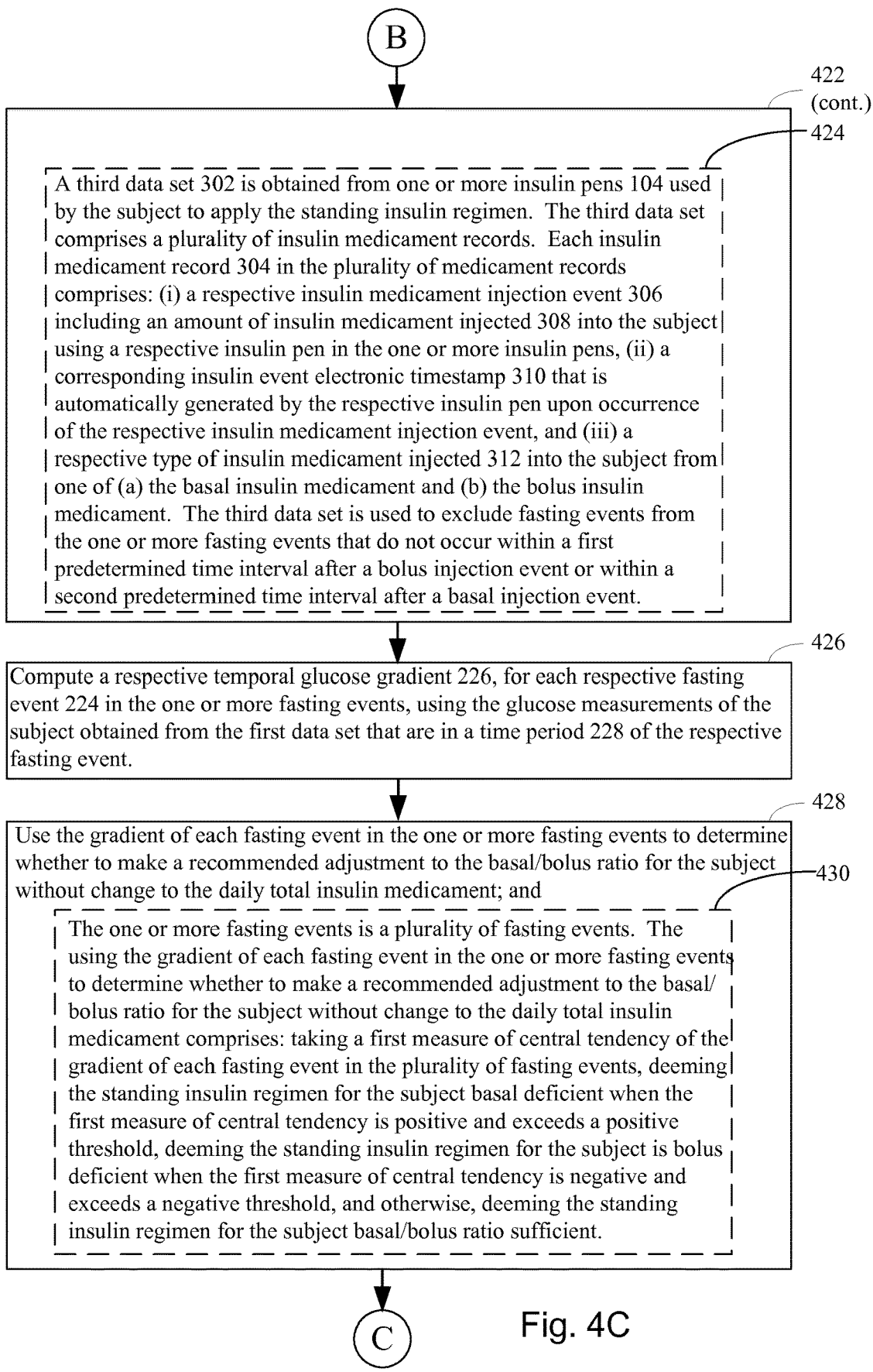
Figure 4E:
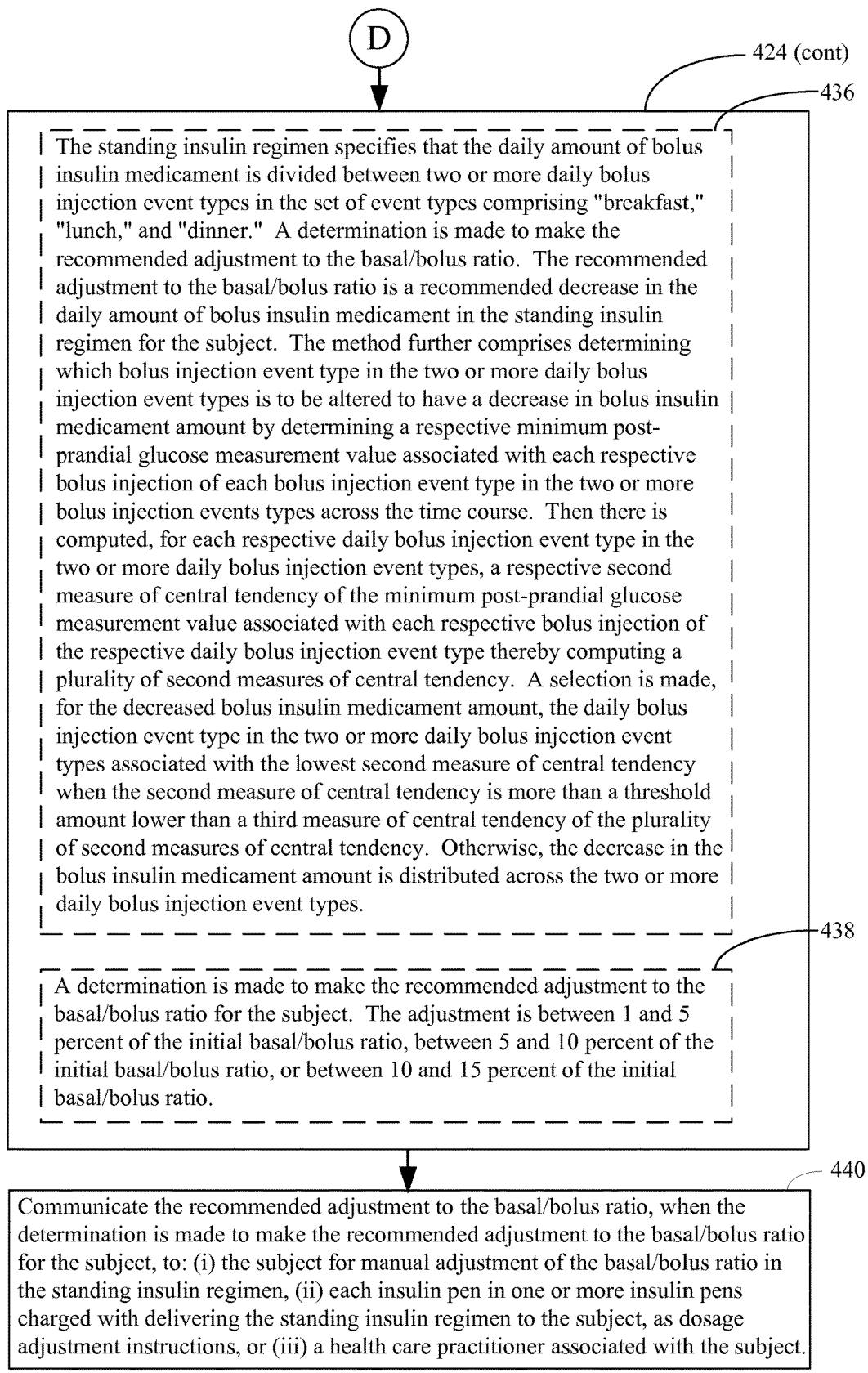

For instance, referring to block 430 of FIG. 4C, in some embodiments, the one or more fasting events constitute a plurality of fasting events. In such embodiments, the temporal glucose gradient 226 of each fasting event 224 in the one or more fasting events is used to determine whether to make a recommended adjustment to the basal/bolus ratio for the subject without change to the daily total insulin medicament by taking a first measure of central tendency of the temporal glucose gradient 226 of each fasting event 224 in the plurality of fasting events. In some embodiments, the measure of central tendency of the temporal glucose gradient 226 of each fasting event 224 in the plurality of fasting events can be, for example, an arithmetic mean, weighted mean, midrange, midhinge, trimean, Winsorized mean, median, or mode of the temporal glucose gradients 226. The standing insulin regimen 206 for the subject is deemed to be basal insulin medicament deficient when this first measure of central tendency is positive and exceeds a positive threshold. In some embodiments, the positive threshold is a value of three percent, a value of four percent, a value of five percent, or a value of ten percent or greater. In some embodiments, the positive threshold is optimized for each subject based upon characteristics of the subject. As an example, if the measure of central tendency is a simple average and the positive threshold is three percent, this means that on average, the temporal glucose gradient 226 is a positively sloped line of three percent or greater, using the frame of reference of FIG. 7, panel A. Continuing with the example, the standing insulin regimen for the subject is deemed bolus deficient when the first measure of central tendency is negative and exceeds a negative threshold. In some embodiments, the negative threshold is a value of minus three percent, a value of minus four percent, a value of minus five percent, or a value of minus ten percent or less. In some embodiments, the negative threshold is optimized for each subject based upon characteristics of the subject.

As an example, if the measure of central tendency is a simple average and the negative threshold is minus three percent, this means that on average, the temporal glucose gradient 226 is a negatively sloped line of three percent or less (larger degrees of negative slope), using the frame of reference of FIG. 7, panel B. If the standing insulin regimen for the subject is not deemed basal or bolus deficient, it is deemed basal/bolus ratio sufficient the basal/bolus ratio is not adjusted.

Referring to block 432 of FIG. 4D, in some embodiments, the one or more fasting events is a single fasting event. In such embodiments, the use of the temporal glucose gradient 226 of each fasting event 224 in the one or more fasting events to determine whether to make a recommended adjustment to the basal/bolus ratio for the subject without change to the daily total insulin medicament set forth in block 428 comprises: deeming the standing insulin regimen 206 for the subject basal deficient when the temporal glucose gradient 226 of the single fasting event 222 is positive and exceeds the positive threshold discussed above for block 430, deeming the standing insulin regimen 206 for the subject bolus deficient when the temporal glucose gradient 226 of the single fasting event is negative and exceeds the negative threshold discussed above for block 430, and otherwise, deeming the standing insulin regimen 206 for the subject basal/bolus ratio sufficient (and therefore not adjusting the basal/bolus ratio).

Block 434. Block 434 of FIG. 4D describes a specific embodiment of the present disclosure. In this embodiment, the standing insulin regimen 206 specifies that the daily amount of bolus insulin medicament is divided between two or more daily bolus injection event types in the set of event types comprising "breakfast," "lunch," and "dinner." Further, the determination is made to make the recommended adjustment to the basal/bolus ratio (e.g., in accordance with block 428, 430, or 432). Here, the recommended adjustment to the basal/bolus ratio is a recommended increase in the daily amount of bolus insulin medicament in the standing insulin regimen 206 for the subject. In this embodiment, the method further comprises determining which bolus injection event type in the two or more daily bolus injection event types is to be altered to have an increased bolus insulin medicament amount by determining a respective minimum post-prandial glucose measurement value associated with each respective bolus injection of each bolus injection event type in the two or more bolus injection events types across the time course. For instance, for the particular bolus injection event type "breakfast," the glucose measurements 218 for the period of time after each breakfast (e.g., up to 5 minutes after, up to fifteen minutes after, up to 30 minutes, up to 1 hour after the breakfast) is polled for a minimum post-prandial glucose measurement value associated with each breakfast. Then there is computed, for each respective daily bolus injection event type in the two or more daily bolus injection event types, a respective second measure of central tendency of the minimum post-prandial glucose measurement value associated with each respective bolus injection of the respective daily bolus injection event type thereby computing a plurality of second measures of central tendency. Thus, continuing with the example above, a measure of central tendency of the minimum post-prandial glucose measurement value associated with each breakfast is taken. Likewise, a measure of central tendency of the minimum post-prandial glucose measurement value associated with each lunch is taken. Further, a measure of central tendency of the minimum post-prandial glucose measurement value associated with each dinner is taken. This measure of central tendency can be, for example, an arithmetic mean, weighted mean, midrange, midhinge, trimean, Winsorized mean, median, or mode of the minimum post-prandial glucose measurement value associated with a given event type (e.g., breakfast, lunch or dinner). Further, there is selected, for the increased bolus insulin medicament amount, the daily bolus injection event type in the two or more daily bolus injection event types associated with the highest second measure of central tendency when the second measure of central tendency is more than a threshold amount higher than a third measure of central tendency of the plurality of second measures of central tendency. For instance, consider the case where there are three event types, breakfast, lunch and dinner. Thus, there are three second measures of central tendency, respectively representing the minimum post-prandial glucose measurement value associated with each event type. A measure of central tendency is taken of these three values and this constitutes the third measure of central tendency. This third measure of central tendency can be, for example, an arithmetic mean, weighted mean, midrange, midhinge, trimean, Winsorized mean, median, or mode of the second measures of central tendency. If the highest second measure of central tendency is greater than a threshold amount than the third measure of central tendency, the daily bolus injection event type in the two or more daily bolus injection event types associated with the highest second measure of central tendency is selected, for the increased bolus insulin medicament amount. Otherwise, the increase in the bolus insulin medicament amount is distributed across the two or more daily bolus injection event types (e.g. proportional to their associated minimum post-prandial glucose measurement values, equally, etc.). Here, in some embodiments, the requisite threshold amount for the second measure of central tendency is application specific and may be different for each subject. In some embodiments, the requisite threshold amount the second measure of central tendency must be is ten percent larger, twenty percent or larger, or thirty percent larger than the third measure of central tendency.

Block 436. Block 436 of FIG. 4E describes another specific embodiment of the present disclosure. In this embodiment, the standing insulin regimen 206 specifies that the daily amount of bolus insulin medicament is divided between two or more daily bolus injection event types in the set of event types comprising "breakfast," "lunch," and "dinner." A determination is made to make the recommended adjustment to the basal/bolus ratio (e.g., in accordance with block 428, 430, or 432). Contrary to block 434, the recommended adjustment to the basal/bolus ratio is a recommended decrease in the daily amount of bolus insulin medicament in the standing insulin regimen 206 for the subject. In this embodiment, the method further comprises determining which bolus injection event type in the two or more daily bolus injection event types is to be altered to have a decrease in bolus insulin medicament amount by determining a respective minimum post-prandial glucose measurement value associated with each respective bolus injection of each bolus injection event type in the two or more bolus injection events types across the time course. For instance, for the particular bolus injection event type "breakfast," the glucose measurements 218 for the period of time after each breakfast (e.g., up to 5 minutes after, up to fifteen minutes after, up to 30 minutes, up to 1 hour after the breakfast) is polled for a minimum post-prandial glucose measurement value associated with each breakfast. Then there is computed, for each respective daily bolus injection event type in the two or more daily bolus injection event types, a respective second measure of central tendency of the minimum post-prandial glucose measurement value associated with each respective bolus injection of the respective daily bolus injection event type thereby computing a plurality of second measures of central tendency. Thus, continuing with the example above, a measure of central tendency of the minimum post-prandial glucose measurement value associated with each breakfast in the time course is taken. Likewise, a measure of central tendency of the minimum post-prandial glucose measurement value associated with each lunch is taken. Further, a measure of central tendency of the minimum post-prandial glucose measurement value associated with each dinner is taken. This measure of central tendency can be, for example, an arithmetic mean, weighted mean, midrange, midhinge, trimean, Winsorized mean, median, or mode of the minimum post-prandial glucose measurement value associated with a given event type (e.g., breakfast, lunch or dinner). Further, there is selected, for the decreased bolus insulin medicament amount, the daily bolus injection event type in the two or more daily bolus injection event types associated with the lowest second measure of central tendency when the second measure of central tendency for this event type is more than a threshold amount lower than a third measure of central tendency of the plurality of second measures of central tendency. For instance, consider the case where there are three event types, breakfast, lunch and dinner. Thus, there are three second measures of central tendency, respectively representing the minimum post-prandial glucose measurement value associated with each event type. A measure of central tendency is taken of these three values and this constitutes the third measure of central tendency. This third measure of central tendency can be, for example, an arithmetic mean, weighted mean, midrange, midhinge, trimean, Winsorized mean, median, or mode of the second measures of central tendency. If the lowest second measure of central tendency is more than a threshold amount lower than the third measure of central tendency, the daily bolus injection event type in the two or more daily bolus injection event types associated with the lowest second measure of central tendency is selected, for the decreased bolus insulin medicament amount. Otherwise, the decrease in the bolus insulin medicament amount is distributed across the two or more daily bolus injection event types (e.g. proportional to their associated minimum post-prandial glucose measurement values, equally, etc.). Here, in some embodiments, the requisite threshold amount for the second measure of central tendency is application specific and may be different for each subject. In some embodiments, the requisite threshold amount the second measure of central tendency must be is more than ten percent larger, twenty percent or larger, or thirty percent lower than the third measure of central tendency.

Block 438. Referring to block 438, the method continues when a determination is made to make the recommended adjustment to the basal/bolus ratio for the subject (e.g., the standing insulin regimen 206 for the subject is deemed basal or bolus deficient). In some such embodiments, the adjustment is between 1 and 5 percent of the initial basal/bolus ratio, between 5 and 10 percent of the initial basal/bolus ratio, or between 10 and 15 percent of the initial basal/bolus ratio. In some embodiments, rather than relying upon a basal/bolus ratio in accordance with standing insulin regimen as the starting point to make this adjustment, the actual administered basal/bolus ratio is computed using the insulin medicament records in the third data set 302. In some such embodiments, the insulin medicament records in the third data set 302 from the past day, the past two days, the past three days, the past week, or the past two weeks is used to compute the actual basal/bolus and then, in block 438, when a determination is made to make the recommended adjustment to the basal/bolus ratio for the subject, the adjustment is between 1 and 5 percent of the initial basal/bolus ratio, between 5 and 10 percent of the initial basal/bolus ratio, or between 10 and 15 percent of the calculated basal/bolus ratio.

Figure 8:
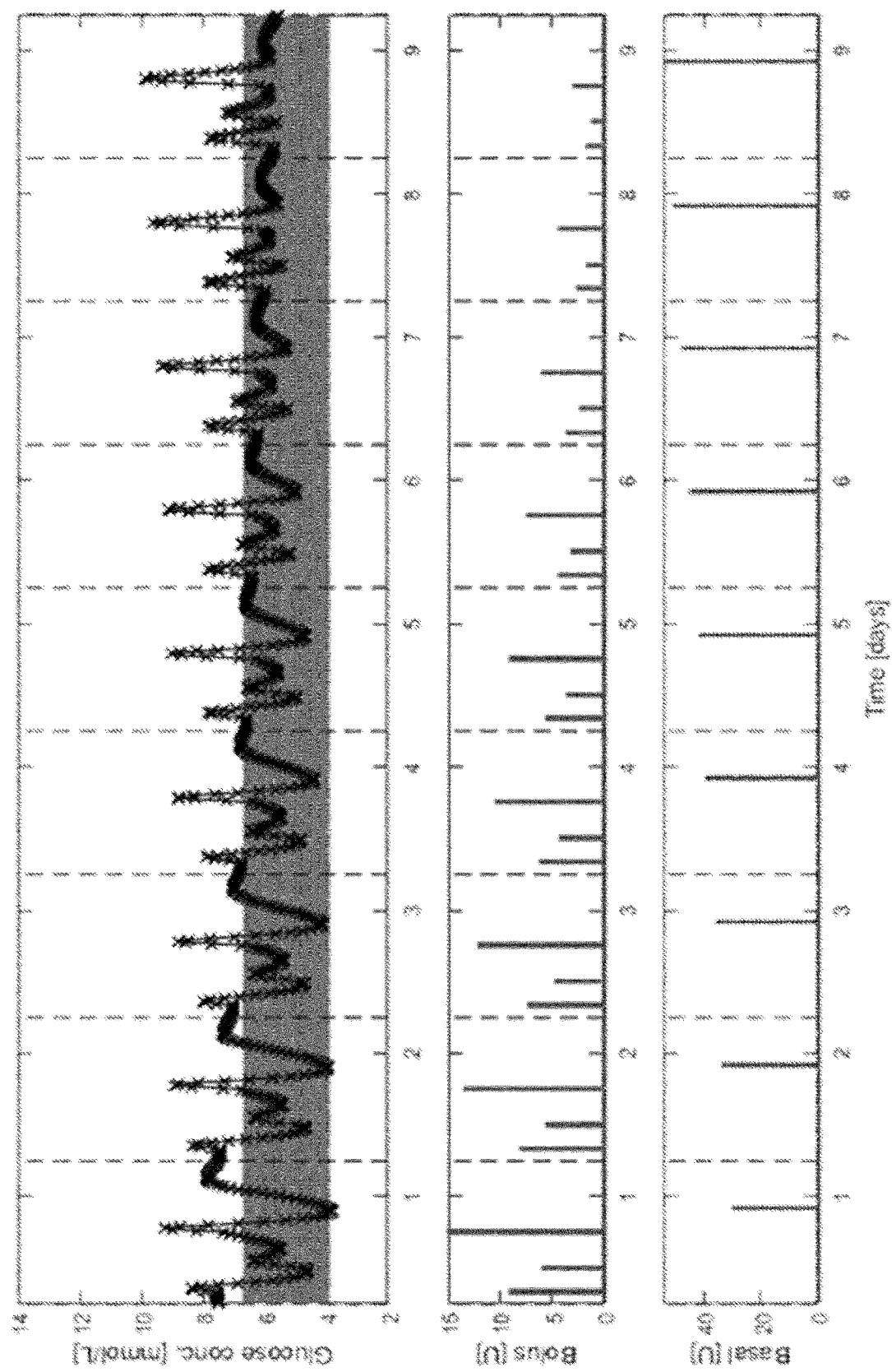
FIG. 8 illustrates determining the ratio between basal and bolus dosage, in which the top panel shows blood glucose concentration over nine days, the middle panel shows bolus injections during this time course, and the bottom panel shows the basal injections during this time course. The ratio-algorithm starts assuming 60 IU in total, and splits basal/bolus 50%/50%. Breakfast/lunch/dinner boluses are divided 30%/20%/50% of bolus insulin. The ratio between basal/bolus is changed according to the calculated gradient over the fasting period, which in this case is defined to start four hours after dinner until breakfast in accordance with an example embodiment of the present disclosure.
Figure 9:
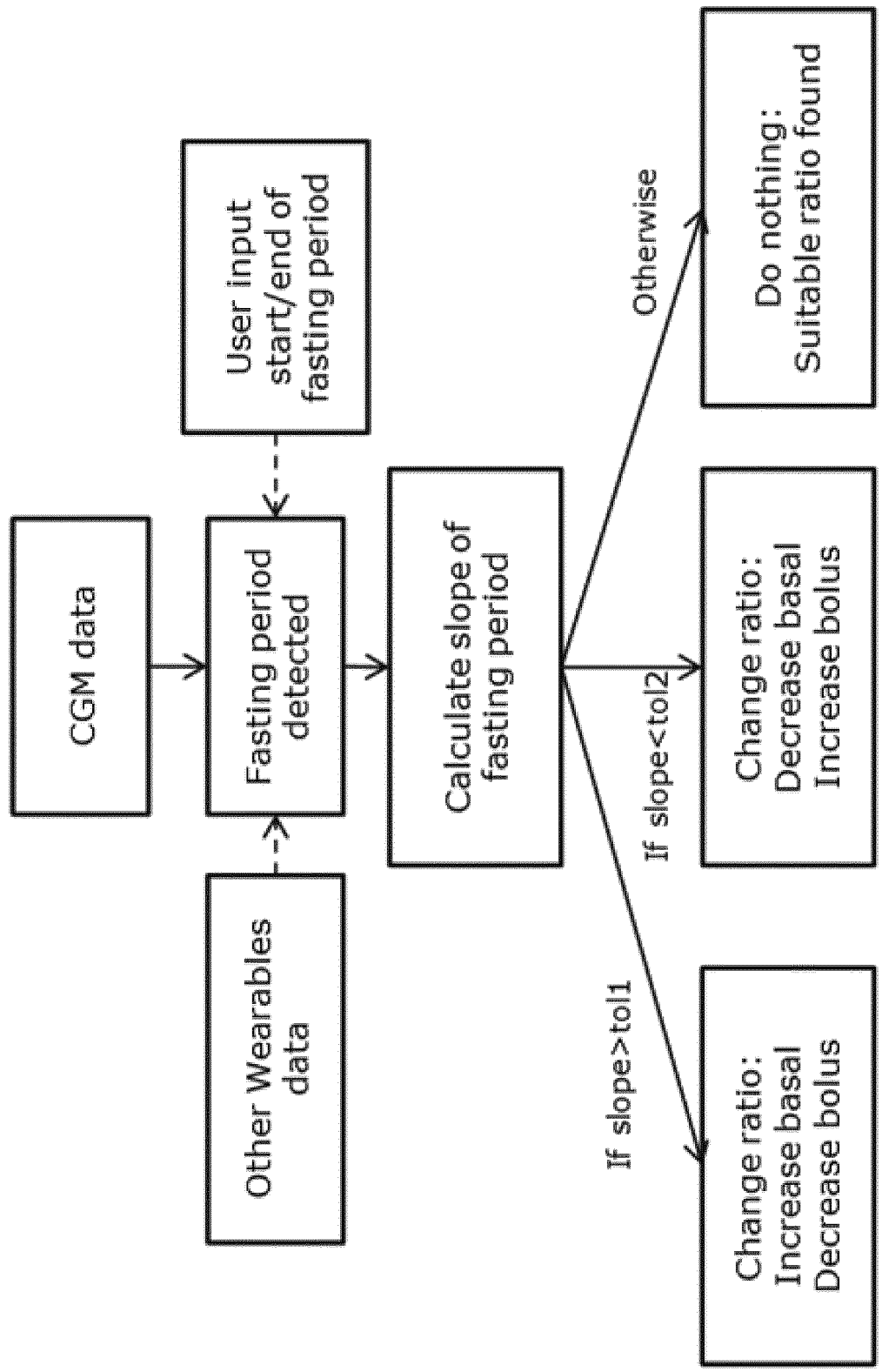
FIG. 9 illustrates an exemplary algorithm for adjusting a basal/bolus ratio in a standing insulin regimen for a subject in accordance with an embodiment of the present disclosure.

Block 440. Referring to block 440 of FIG. 4E, the method continues by communicating the recommended adjustment to the basal/bolus ratio, when the determination is made to make the recommended adjustment to the basal/bolus ratio for the subject, to: (i) the subject for manual adjustment of the basal/bolus ratio in the standing insulin regimen 206, (ii) each insulin pen 104 in one or more insulin pens charged with delivering the standing insulin regimen 206 to the subject, as dosage adjustment instructions, or (iii) a health care practitioner associated with the subject. FIG. 9 illustrates an exemplary embodiment of the method disclosed in FIGS. 4A through 4E while FIG. 8 illustrates the administration of basal and bolus insulin medicaments to a subject in accordance with a standing insulin regimen 206 over the time course and the resultant glucose concentration of the subject over this time course.

Example 1: Use of glucose measurements to determine whether a fasting event is insulin regimen adherent. In some embodiments, the first data set 216 comprising a plurality of glucose measurements is obtained. In some embodiments the glucose measurements are obtained autonomously, for instance by a continuous glucose monitor 102. In this example, in addition to the autonomous glucose measurements, insulin administration events are obtained in the form of insulin medicament injection events 306 from one or more insulin pens 104 used by the subject to apply the standing insulin regimen 206. These insulin medicament records 304 may be in any format, and in fact may be spread across multiple files or data structures. As such, in some embodiments, the instant disclosure leverages the recent advances of insulin administration pens, which have become "smart" in the sense that they can remember the timing and the amount of insulin medicament administered in the past. One example of such an insulin pen 104 is the NovoPen 5. Such pens assists patients in logging doses and prevent double dosing. It is contemplated that insulin pens will be able to send and receive insulin medicament dose volume and timing, thus allowing the integration of continuous glucose monitors 102, insulin pens 104 and the algorithms of the present disclosure. As such, insulin medicament records 304 from one or more insulin pens 104 is contemplated, including the wireless acquisition of such data from the one or more insulin pens 104.

In some embodiments, each insulin medicament record 304 comprises: (i) a respective insulin medicament injection event 306 including an amount of insulin medicament injected 308 into the subject using a respective insulin pen 104 in the one or more insulin pens and (ii) a corresponding insulin event electronic timestamp 310 that is automatically generated by the respective insulin pen 104 upon occurrence of the respective insulin medicament injection event 306.

In some embodiments, a fasting event 224 is identified using the glucose measurements 218 of the subject and their associated glucose measurement timestamps 220 in the first data set 216. Once a fasting event is identified, e.g., by a method described in any one of blocks 412-422 above, or any other method, a classification is applied to the fasting event 224. The classification is one of "insulin regimen adherent" and "insulin regimen nonadherent."

A fasting event 224 is deemed insulin regimen adherent when the acquired one or more medicament records 304 establish, on a temporal and quantitative basis, adherence with the basal insulin medicament regimen 208 during the fasting event 224. A fasting event 224 is deemed insulin regimen nonadherent when the acquired one or more medicament records 304 do not include one or more medicament records that establish, on a temporal and quantitative basis, adherence with the basal insulin medicament dosage regimen 208 during the fasting event 224. In some embodiments, the basal insulin medicament dosage regimen 208 specifies that a dosage of the basal insulin medicament is to be taken during each respective epoch (e.g., day, twelve hour period) in a plurality of epochs and that a fasting event 224 is deemed insulin regimen nonadherent when there are no insulin medicament records 304 for the epoch associated with the fasting event 224. In various embodiments, each epoch in the plurality of epochs is two days or less, one day or less, or 12 hours or less. Thus, consider the case where the first data set 216 is used to identify a fasting event 224 and the basal insulin medicament dosage regimen 208 specifies to take dosage A of a basal insulin medicament every 24 hours. In this example, therefore, the epoch is one day (24 hours). The fasting event 224 is inherently timestamped because it is derived from a period of minimum variance in timestamped glucose measurements, or by other forms of analysis of the timestamped glucose measurements 218. Thus, the glucose measurement timestamp, or period of fasting (fasting event time period 228), represented by a respective fasting event 224 is used as a starting point for examining whether the fasting event is insulin regimen adherent. For instance, if the period of fasting associated with the respective timestamp includes 6:00 AM on Tuesday, May 17, what is sought in the insulin medicament records 304 is evidence that the subject took dosage A of the basal insulin medicament in the 24 hour period (the epoch) leading up to 6:00 AM on Tuesday, May 17 (and not more or less of the prescribed dosage). If the subject took the prescribed dosage of the basal insulin medicament during this epoch, the fasting event is deemed insulin regimen adherent. If the subject did not take the dose of the basal insulin medicament 216 during this epoch (or took more than the dose of the basal insulin medicament during this period specified by the basal insulin medicament dosage regimen 208), the fasting event 224 is deemed to be insulin regimen nonadherent.

In some embodiments, the epoch is defined by the basal insulin medicament dosage regimen 208 and, so long as the subject took the amount of basal insulin medicament required by the basal insulin medicament dosage regimen 208 during the epoch (and not more), even if after the fasting event 224, the fasting event will be deemed insulin regimen adherent. For instance, if the epoch is one day beginning each day at just after midnight (in other words the basal insulin medicament dosage regimen 208 specifies one or more basal insulin medicament dosages to be taken each day, and further defines a day as beginning and ending at midnight), and the fasting event 224 occurs at noon (e.g., for a 10 minute period centered at noon), the fasting event 224 will be deemed insulin regimen adherent provided that the subject takes the basal insulin medicament injections prescribed for the day at some point during the day.

List of Embodiments

1. A device 250 for adjusting a basal/bolus ratio in a standing insulin regimen for a subject, wherein the device comprises one or more processors 274 and a memory 192/290, the memory storing instructions that, when executed by the one or more processors, perform a method of:

obtaining the standing insulin regimen 206 for the subject, wherein the standing insulin regimen for the subject comprises a daily total insulin medicament, the daily total insulin medicament is satisfied by a combination of a daily amount of a basal insulin medicament 210 and a daily amount of a bolus insulin medicament 214 specified by the standing insulin regimen for the subject that is administered by one or more insulin pens, and the daily amount of basal insulin medicament and the daily amount of bolus insulin medicament defines an initial basal/bolus ratio between the daily amount of basal insulin medicament and the daily amount of bolus insulin medicament;

obtaining a first data set 216, the first data set comprising a plurality of glucose measurements of the subject over a time course, and, for each respective glucose measurement 218 in the plurality of glucose measurements, a timestamp representing when the respective measurement was made;

identifying one or more fasting events in the time course;

computing a respective temporal glucose gradient 226, for each respective fasting event 224 in the one or more fasting events, using the glucose measurements of the subject obtained from the first data set that are in a time period 228 of the respective fasting event;

using the gradient of each fasting event in the one or more fasting events to determine whether to make a recommended adjustment to the basal/bolus ratio for the subject without change to the daily total insulin medicament; and communicating the recommended adjustment to the basal/bolus ratio, when the determination is made to make the recommended adjustment to the basal/bolus ratio for the subject, to:

(i) the subject for manual adjustment of the basal/bolus ratio in the standing insulin regimen, (ii) each insulin pen in the one or more insulin pens charged with delivering the standing insulin regimen to the subject, as dosage adjustment instructions, or (iii) a health care practitioner associated with the subject.

2. The device of embodiment 1, wherein the standing insulin regimen for the subject further comprises a post-prandial glucose target, and a correction bolus to account for a post-prandial glucose level above the post-prandial glucose target, wherein the correction bolus is specified to be administered by the one or more insulin pens.

3. The device of any of embodiments 1 or 2, wherein the standing insulin regimen for the subject further comprises a lower range glucose target, and a carbohydrate correction to account for a glucose level below the lower range glucose target, wherein the carbohydrate correction can be administered orally.

4. The device of any of embodiments 1 to 3, wherein
the one or more fasting events is a plurality of fasting events,
the using the gradient of each fasting event in the one or more fasting events to determine whether to make a recommended adjustment to the basal/bolus ratio for the subject without change to the daily total insulin medicament comprises:
  taking a first measure of central tendency of the gradient of each fasting event in the plurality of fasting events,
  deeming the standing insulin regimen for the subject basal deficient when the first measure of central tendency is positive and exceeds a positive threshold,
  deeming the standing insulin regimen for the subject is bolus deficient when the first measure of central tendency is negative and exceeds a negative threshold, and
  otherwise, deeming the standing insulin regimen for the subject basal/bolus ratio sufficient.

5. The device of any of embodiments 1-3, wherein
the one or more fasting events is a single fasting event, and wherein
the using the gradient of each fasting event in the one or more fasting events to determine whether to make a recommended adjustment to the basal/bolus ratio for the subject without change to the daily total insulin medicament comprises:
  deeming the standing insulin regimen for the subject basal deficient when the gradient of the single fasting event is positive and exceeds a positive threshold,
  deeming the standing insulin regimen for the subject bolus deficient when the gradient of the single fasting event is negative and exceeds a negative threshold, and
  otherwise, deeming the standing insulin regimen for the subject basal/bolus ratio sufficient.

6. The device of any one of embodiments 1-5, wherein each glucose measurements in the plurality of glucose measurements is autonomously measured and the one or more fasting events are determined using the plurality of glucose measurements of the subject and the respective timestamps in the first data set.

7. The device of embodiment 6, wherein the identifying the plurality of fasting events comprises identifying a first fasting period in a first time period encompassed by the time course by:
computing a moving period of variance $\sigma_k^2$ across the plurality of glucose measurements, wherein:

$$\sigma_k^2 = \frac{1}{M} \sum_{i=k-M}^{k} (G_i - \overline{G})^2$$

wherein,
  $G_i$ is the $i^{th}$ glucose measurement in a portion of the plurality of glucose measurements,
  M is a number of glucose measurements in the plurality of glucose measurements and represents a contiguous predetermined time span,
  $\overline{G}$ is the mean of the glucose measurements selected from the plurality of glucose measurements, and
  k is within the first time period; and
associating the first fasting period with a period of minimum variance $_k^{min}\sigma_k^2$ within the first time period.

8. The device of any one of embodiments 1-6, wherein the identifying the one or more fasting events comprises receiving an indication of each fasting event in the one or more fasting events from the subject.

9. The device of any one of embodiments 1-6, wherein
the identifying the one or more fasting events comprises receiving a second data set (220) from a wearable device worn by the subject, and
the second data set indicates a physiological metric 232 of the user during the time course that is indicative of the one or more fasting events.

10. The device of any of embodiments 1 to 4, wherein
the standing insulin regimen specifies that the daily amount of bolus insulin medicament is divided between two or more daily bolus injection event types in the set of event types comprising "breakfast," "lunch," and "dinner,"
a determination is made to make the recommended adjustment to the basal/bolus ratio,
the recommended adjustment to the basal/bolus ratio is a recommended increase in the daily amount of bolus insulin medicament in the standing insulin regimen for the subject, and the method further comprises:
  determining which bolus injection event type in the two or more daily bolus injection event types is to be altered to have an increased bolus insulin medicament amount by:
  determining a respective minimum post-prandial glucose measurement value associated with each respective bolus injection of each bolus injection event type in the two or more bolus injection events types across the time course;
  computing, for each respective daily bolus injection event type in the two or more daily bolus injection event types, a respective second measure of central tendency of the minimum post-prandial glucose measurement value associated with each respective bolus injection of the respective daily bolus injection event type thereby computing a plurality of second measures of central tendency, and
  selecting, for the increased bolus insulin medicament amount, the daily bolus injection event type in the two or more daily bolus injection event types associated with the highest second measure of central tendency when the second measure of central tendency is more than a threshold amount higher than a third measure of central tendency of the plurality of second measures of central tendency and distributing the increase in the bolus insulin medicament amount across the two or more daily bolus injection event types otherwise.

11. The device of any of embodiments 1 to 4, wherein
the standing insulin regimen specifies that the daily amount of bolus insulin medicament is divided between two or more daily bolus injection event types in the set of event types comprising "breakfast," "lunch," and "dinner,"
a determination is made to make the recommended adjustment to the basal/bolus ratio,
the recommended adjustment to the basal/bolus ratio is a recommended decrease in the daily amount of bolus insulin medicament in the standing insulin regimen for the subject, and the method further comprises:
  determining which bolus injection event type in the two or more daily bolus injection event types is to be altered to have a decrease in bolus insulin medicament amount by:

determining a respective minimum post-prandial glucose measurement value associated with each respective bolus injection of each bolus injection event type in the two or more bolus injection events types across the time course;

computing, for each respective daily bolus injection event type in the two or more daily bolus injection event types, a respective second measure of central tendency of the minimum post-prandial glucose measurement value associated with each respective bolus injection of the respective daily bolus injection event type thereby computing a plurality of second measures of central tendency, and selecting, for the decreased bolus insulin medicament amount, the daily bolus injection event type in the two or more daily bolus injection event types associated with the lowest second measure of central tendency when the second measure of central tendency is more than a threshold amount lower than a third measure of central tendency of the plurality of second measures of central tendency and distributing the decrease in the bolus insulin medicament amount across the two or more daily bolus injection event types otherwise.

12. The device of any one of embodiments 1-11, the method further comprising:

obtaining a third data set 302 from one or more insulin pens 104 used by the subject to apply the standing insulin regimen, the third data set comprising a plurality of insulin medicament records, each insulin medicament record 304 in the plurality of medicament records comprising: (i) a respective insulin medicament injection event 306 including an amount of insulin medicament injected 308 into the subject using a respective insulin pen in the one or more insulin pens, (ii) a corresponding insulin event electronic timestamp 310 that is automatically generated by the respective insulin pen upon occurrence of the respective insulin medicament injection event, and (iii) a respective type of insulin medicament injected 312 into the subject from one of (a) the basal insulin medicament and (b) the bolus insulin medicament, and using the third data set to exclude fasting events from the one or more fasting events that do not occur within a first predetermined time interval after a bolus injection event or within a second predetermined time interval after a basal injection event.

13. The device of any of the previous embodiments, wherein the one or more fasting events are within the last week, within the last two weeks, or within the last month and wherein the method is repeated on a recurring basis over time.

14. The device of any one of embodiments 1-13, wherein a determination is made to make the recommended adjustment to the basal/bolus ratio for the subject, and the adjustment is between 1 and 5 percent of the initial basal/bolus ratio, between 5 and 10 percent of the initial basal/bolus ratio, or between 10 and 15 percent of the initial basal/bolus ratio.

15. The device of any one of embodiments 1-14, wherein the device further comprises a wireless receiver, and the first data set is obtained wirelessly from a glucose sensor affixed to the subject.

16. The device of any one of embodiments 1-15, wherein the basal insulin medicament consists of a single insulin medicament having a duration of action that is between 12 and 24 hours or a mixture of insulin medicaments that collectively have a duration of action that is between 12 and 24 hours, and the bolus insulin medicament consists of a single insulin medicament having a duration of action that is between three to eight hours or a mixture of insulin medicaments that collectively have a duration of action that is between three to eight hours.

17. A method for adjusting a basal/bolus ratio in a standing insulin regimen for a subject, the method comprising:

at a computer system comprising one or more processors and a memory:

obtaining the standing insulin regimen 206 for the subject, wherein the standing insulin regimen for the subject comprises a daily total insulin medicament, the daily total insulin medicament is satisfied by a combination of a daily amount of a basal insulin medicament 210 and a daily amount of a bolus insulin medicament 214 specified by the standing insulin regimen for the subject that is administered by one or more insulin pens, and the daily amount of basal insulin medicament and the daily amount of bolus insulin medicament defines an initial basal/bolus ratio between the daily amount of basal insulin medicament and the daily amount of bolus insulin medicament;

obtaining a first data set 216, the first data set comprising a plurality of glucose measurements of the subject over a time course, and, for each respective glucose measurement 218 in the plurality of glucose measurements, a timestamp 220 representing when the respective measurement was made;

identifying one or more fasting events in the time course;

computing a respective temporal glucose gradient 226, for each respective fasting event 224 in the one or more fasting events, using the glucose measurements of the subject obtained from the first data set that are in a time period 228 of the respective fasting event;

using the gradient of each fasting event in the one or more fasting events to determine whether to make a recommended adjustment to the basal/bolus ratio for the subject without change to the daily total insulin medicament; and communicating the recommended adjustment to the basal/bolus ratio, when the determination is made to make the recommended adjustment to the basal/bolus ratio for the subject, to:

(i) the subject for manual adjustment of the basal/bolus ratio in the standing insulin regimen, (ii) each insulin pen in the one or more insulin pens charged with delivering the standing insulin regimen to the subject, as dosage adjustment instructions, or (iii) a health care practitioner associated with the subject.

18. A computer program comprising instructions that, when executed by one or more processors, perform the method of embodiment 17.

19. A computer-readable data carrier having stored thereon the computer program according to embodiment 18.

References Cited and Alternative Embodiments

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIGS. 1, 2, 3, 5 and/or described in FIG. 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:

1. A device for adjusting a basal/bolus ratio in a standing insulin regimen for a subject, wherein the device comprises one or more processors and a memory, the memory storing instructions that, when executed by the one or more processors, perform the method of:
   obtaining the standing insulin regimen for the subject, wherein the standing insulin regimen is specific for the subject and comprises a daily total insulin medicament, the daily total insulin medicament is satisfied by a combination of a daily amount of a basal insulin medicament and a daily amount of a bolus insulin medicament specified by the standing insulin regimen for the subject that is administered by one or more insulin pens, and the daily amount of basal insulin medicament and the daily amount of bolus insulin medicament defines an initial basal/bolus ratio between the daily amount of basal insulin medicament and the daily amount of bolus insulin medicament;
   determining and storing the initial basal/bolus ratio;
   obtaining a first data set, the first data set comprising a plurality of glucose measurements of the subject over a time course, wherein the time course encompasses a first fasting period in a first time period, and, for each respective glucose measurement in the plurality of glucose measurements, a timestamp representing when the respective measurement was made;
   identifying a plurality of fasting events in the first fasting period of the time course;
   computing iteratively, for each respective fasting event in the plurality of fasting events, a respective minimum temporal glucose gradient uniquely associated with said each respective fasting event in the plurality of fasting events, using the glucose measurements of the subject obtained from the first data set that are in the first fasting period of the respective fasting event;
   using the minimum gradient of each fasting event in the plurality of fasting events to make a recommended adjustment to the standing insulin regimen by controlling the basal/bolus ratio for the subject while maintaining the daily total insulin medicament at a constant level,
   wherein the using the minimum gradient of each fasting event in the plurality of fasting events to determine whether to make a recommended adjustment to the basal/bolus ratio for the subject while maintaining the daily total insulin medicament comprises:
      defining or accessing a positive threshold and a negative threshold,
      taking a first measure of central tendency of the gradient of each fasting event in the plurality of fasting events, wherein the measure of central tendency taken is one of an arithmetic mean, a weighted mean, a midrange, a midhinge, a trimean, a Winsorized mean, a median, or a mode of the temporal glucose gradients of the plurality of fasting events,
      deeming the standing insulin regimen for the subject basal deficient when the first measure of central tendency is positive and exceeds a positive threshold,
      deeming the standing insulin regimen for the subject is bolus deficient when the first measure of central tendency is negative and exceeds a negative threshold, and
      otherwise, deeming the standing insulin regimen for the subject basal/bolus ratio sufficient;
   in response to deeming the standing insulin regimen for the subject is basal deficient, communicating the recommended adjustment to the basal/bolus ratio, to make the recommended adjustment to the basal/bolus ratio for the subject, to:
      (i) the subject for manual adjustment of the basal/bolus ratio in the standing insulin regimen,
      (ii) each insulin pen in the one or more insulin pens charged with delivering the standing insulin regimen to the subject, as dosage adjustment instructions, or
      (iii) a health care practitioner associated with the subject; and
   controlling the one or more insulin pens to administer, by the one or more insulin pens, at least one dose of an adjusted standing insulin regimen based on the recommended adjustment.

2. The device of claim 1, wherein the standing insulin regimen for the subject further comprises a post-prandial glucose target and a correction bolus to account for a post-prandial glucose level above the post-prandial glucose target, wherein the correction bolus is specified to be administered by the one or more insulin pens.

3. The device of claim 1, wherein the standing insulin regimen for the subject further comprises a lower range glucose target and a carbohydrate correction to account for a glucose level below the lower range glucose target, wherein the carbohydrate correction can be administered orally.

4. The device of claim 1, wherein each glucose measurement in the plurality of glucose measurements is autonomously measured and the plurality of fasting events are determined using the plurality of glucose measurements of the subject and the respective timestamps in the first data set.

5. The device of claim 4, wherein the identifying the plurality of fasting events comprises identifying the first fasting period in the first time period encompassed by the time course by:
   computing a moving period of variance $\sigma_k^2$ across the plurality of glucose measurements, wherein $$\sigma_k^2 = \frac{1}{M} \sum_{i=k-M}^{k} (G_i - \overline{G})^2$$

wherein,
- $G_i$ is the $i^{th}$ glucose measurement in a portion k of the plurality of glucose measurements,
- M is a number of glucose measurements in the plurality of glucose measurements and represents a contiguous predetermined time span,
- $\overline{G}$ is the mean of the glucose measurements selected from the plurality of glucose measurements, and
- k is within the first time period; and associating the first fasting period with a period of minimum variance $_k{}^{min}\sigma_k{}^2$ within the first time period.

6. The device of claim 1, wherein the identifying the plurality of fasting events comprises receiving an indication of each fasting event in the plurality of fasting events from the subject.

7. The device of claim 1, wherein
the identifying the plurality of fasting events comprises receiving a second data set from a wearable device worn by the subject, and
the second data set indicates a physiological metric of the user during the time course that is indicative of the plurality of fasting events.

8. The device of claim 1, the method further comprising:
obtaining a third data set from one or more insulin pens used by the subject to apply the standing insulin regimen, the third data set comprising a plurality of insulin medicament records, each insulin medicament record in the plurality of medicament records comprising: (i) a respective insulin medicament injection event including an amount of insulin medicament injected into the subject using a respective insulin pen in the one or more insulin pens, (ii) a corresponding insulin event electronic timestamp that is automatically generated by the respective insulin pen upon occurrence of the respective insulin medicament injection event, and (iii) a respective type of insulin medicament injected into the subject from one of (a) the basal insulin medicament and (b) the bolus insulin medicament, and
using the third data set to exclude fasting events from the plurality of fasting events that do not occur within a first predetermined time interval after a bolus injection event or within a second predetermined time interval after a basal injection event.

9. The device of claim 1, wherein the plurality of fasting events are within the last week, within the last two weeks, or within the last month and wherein the method is repeated on a recurring basis over time.

10. The device of claim 1, wherein
a determination is made to make the recommended adjustment to the basal/bolus ratio for the subject, and
the adjustment is between 1 and 5 percent of the initial basal/bolus ratio, between 5 and 10 percent of the initial basal/bolus ratio, or between 10 and 15 percent of the initial basal/bolus ratio.

11. The device of claim 1, wherein
the device further comprises a wireless receiver, and
the first data set is obtained wirelessly from a glucose sensor affixed to the subject.

12. The device of claim 1, wherein
the basal insulin medicament consists of a single insulin medicament having a duration of action that is between 12 and 24 hours or a mixture of insulin medicaments that collectively have a duration of action that is between 12 and 24 hours, and
the bolus insulin medicament consists of a single insulin medicament having a duration of action that is between three to eight hours or a mixture of insulin medicaments that collectively have a duration of action that is between three to eight hours.

13. A method for adjusting a basal/bolus ratio in a standing insulin regimen for a subject, the method comprising performing, with
a computer system comprising one or more processors and a memory, steps of:
obtaining the standing insulin regimen for the subject, wherein
the standing insulin regimen is specific for the subject and comprises a daily total insulin medicament,
the daily total insulin medicament is satisfied by a combination of a daily amount of a basal insulin medicament and a daily amount of a bolus insulin medicament specified by the standing insulin regimen for the subject that is administered by one or more insulin pens, and
the daily amount of basal insulin medicament and the daily amount of bolus insulin medicament defines an initial basal/bolus ratio between the daily amount of basal insulin medicament and the daily amount of bolus insulin medicament;
determining and storing the initial basal/bolus ratio;
obtaining a first data set, the first data set comprising a plurality of glucose measurements of the subject over a time course, wherein the time course encompasses a first fasting period in a first time period, and, for each respective glucose measurement in the plurality of glucose measurements, a timestamp representing when the respective measurement was made;
identifying a plurality of fasting events in the first fasting period of the time course;
computing iteratively, for each respective fasting event in the plurality of fasting events, a respective minimum temporal glucose gradient uniquely associated with said each respective fasting event in the plurality of fasting events, using the glucose measurements of the subject obtained from the first data set that are in the first fasting period of the respective fasting event;
using the minimum gradient of each fasting event in the plurality of fasting events to make a recommended adjustment to the standing insulin regimen by controlling the basal/bolus ratio for the subject while maintaining the daily total insulin medicament at a constant level,
wherein the using the minimum gradient of each fasting event in the plurality of fasting events to determine whether to make a recommended adjustment to the basal/bolus ratio for the subject while maintaining the daily total insulin medicament comprises:
defining or accessing a positive threshold and a negative threshold,
taking a first measure of central tendency of the gradient of each fasting event in the plurality of fasting events, wherein the measure of central tendency taken is one of an arithmetic mean, a weighted mean, a midrange, a midhinge, a trimean, a Winsorized mean, a median, or a mode of the temporal glucose gradients of the plurality of fasting events,
deeming the standing insulin regimen for the subject basal deficient when the first measure of central tendency is positive and exceeds a positive threshold,
deeming the standing insulin regimen for the subject is bolus deficient when the first measure of central tendency is negative and exceeds a negative threshold, and otherwise, deeming the standing insulin regimen for the subject basal/bolus ratio sufficient;

in response to deeming the standing insulin regimen for the subject is basal deficient, communicating the recommended adjustment to the basal/bolus ratio, to make the recommended adjustment to the basal/bolus ratio for the subject, to:

(i) the subject for manual adjustment of the basal/bolus ratio in the standing insulin regimen, (ii) each insulin pen in the one or more insulin pens charged with delivering the standing insulin regimen to the subject, as dosage adjustment instructions, or (iii) a health care practitioner associated with the subject; and controlling the one or more insulin pens to administer, by the one or more insulin pens, at least one dose of an adjusted standing insulin regimen based on the recommended adjustment.

14. A non-transitory computer-readable data carrier having stored thereupon a computer program configured to cause a computer system comprising one or more processors and a memory to execute steps of:

obtaining the standing insulin regimen for the subject, wherein the standing insulin regimen is specific for the subject and comprises a daily total insulin medicament, the daily total insulin medicament is satisfied by a combination of a daily amount of a basal insulin medicament and a daily amount of a bolus insulin medicament specified by the standing insulin regimen for the subject that is administered by one or more insulin pens, and the daily amount of basal insulin medicament and the daily amount of bolus insulin medicament defines an initial basal/bolus ratio between the daily amount of basal insulin medicament and the daily amount of bolus insulin medicament;

determining and storing the initial basal/bolus ratio;

obtaining a first data set, the first data set comprising a plurality of glucose measurements of the subject over a time course, wherein the time course encompasses a first fasting period in a first time period, and, for each respective glucose measurement in the plurality of glucose measurements, a timestamp representing when the respective measurement was made;

identifying a plurality of fasting events in the first fasting period of the time course;

computing iteratively, for each respective fasting event in the plurality of fasting events, a respective minimum temporal glucose gradient uniquely associated with said each respective fasting event in the plurality of fasting events, using the glucose measurements of the subject obtained from the first data set that are in the first fasting period of the respective fasting event;

using the minimum gradient of each fasting event in the plurality of fasting events to make a recommended adjustment to the standing insulin regimen by controlling the basal/bolus ratio for the subject while maintaining the daily total insulin medicament at a constant level, wherein the using the minimum gradient of each fasting event in the plurality of fasting events to determine whether to make a recommended adjustment to the basal/bolus ratio for the subject while maintaining the daily total insulin medicament comprises:

defining or accessing a positive threshold and a negative threshold, taking a first measure of central tendency of the gradient of each fasting event in the plurality of fasting events, wherein the measure of central tendency taken is one of an arithmetic mean, a weighted mean, a midrange, a midhinge, a trimean, a Winsorized mean, a median, or a mode of the temporal glucose gradients of the plurality of fasting events, deeming the standing insulin regimen for the subject basal deficient when the first measure of central tendency is positive and exceeds a positive threshold, deeming the standing insulin regimen for the subject is bolus deficient when the first measure of central tendency is negative and exceeds a negative threshold, and otherwise, deeming the standing insulin regimen for the subject basal/bolus ratio sufficient;

in response to deeming the standing insulin regimen for the subject is basal deficient, communicating the recommended adjustment to the basal/bolus ratio, to make the recommended adjustment to the basal/bolus ratio for the subject, to:

(i) the subject for manual adjustment of the basal/bolus ratio in the standing insulin regimen, (ii) each insulin pen in the one or more insulin pens charged with delivering the standing insulin regimen to the subject, as dosage adjustment instructions, or (iii) a health care practitioner associated with the subject; and controlling the one or more insulin pens to administer, by the one or more insulin pens, at least one dose of an adjusted standing insulin regimen based on the recommended adjustment.

15. A device for adjusting a basal/bolus ratio in a standing insulin regimen for a subject, wherein the device comprises one or more processors and a memory, the memory storing instructions that, when executed by the one or more processors, perform a method of:

obtaining the standing insulin regimen for the subject, wherein the standing insulin regimen is specific for the subject and comprises a daily total insulin medicament, the daily total insulin medicament is satisfied by a combination of a daily amount of a basal insulin medicament and a daily amount of a bolus insulin medicament specified by the standing insulin regimen for the subject that is administered by one or more insulin pens, and the daily amount of basal insulin medicament and the daily amount of bolus insulin medicament defines an initial basal/bolus ratio between the daily amount of basal insulin medicament and the daily amount of bolus insulin medicament;

determining and storing the initial basal/bolus ratio;

obtaining a first data set, the first data set comprising a plurality of glucose measurements of the subject over a time course, wherein the time course encompasses a first fasting period in a first time period, and, for each respective glucose measurement in the plurality of glucose measurements, a timestamp representing when the respective measurement was made;

identifying a single fasting event of a plurality of fasting events in the first fasting period of the time course;

computing iteratively, for the single fasting event, a minimum temporal glucose gradient uniquely associated with the single fasting event using the glucose measurements of the subject obtained from the first data set that are in the first fasting period of the single fasting event;

using the minimum gradient of the single fasting event to make a recommended adjustment to the standing insulin regimen by controlling the basal/bolus ratio for the subject while maintaining the daily total insulin medicament at a constant level, wherein the using the minimum gradient of the single fasting event to determine whether to make a recommended adjustment to the basal/bolus ratio for the subject while maintaining the daily total insulin medicament comprises:

defining or accessing a positive threshold and a negative threshold, deeming the standing insulin regimen for the subject basal deficient when the gradient of the single fasting event is positive and exceeds a positive threshold, deeming the standing insulin regimen for the subject is bolus deficient when the gradient of the single fasting event is negative and exceeds a negative threshold, and otherwise, deeming the standing insulin regimen for the subject basal/bolus ratio sufficient;

in response to deeming the standing insulin regimen for the subject basal deficient, communicating the recommended adjustment to the basal/bolus ratio, to make the recommended adjustment to the basal/bolus ratio for the subject, to:

(i) the subject for manual adjustment of the basal/bolus ratio in the standing insulin regimen, (ii) each insulin pen in the one or more insulin pens charged with delivering the standing insulin regimen to the subject, as dosage adjustment instructions, or (iii) a health care practitioner associated with the subject; and controlling the one or more insulin pens to administer, by the one or more insulin pens, at least one dose of an adjusted standing insulin regimen based on the recommended adjustment.

16. The device of claim 15, wherein the standing insulin regimen for the subject further comprises a post-prandial glucose target and a correction bolus to account for a post-prandial glucose level above the post-prandial glucose target, wherein the correction bolus is specified to be administered by the one or more insulin pens.

17. The device of claim 15, wherein the standing insulin regimen for the subject further comprises a lower range glucose target and a carbohydrate correction to account for a glucose level below the lower range glucose target, wherein the carbohydrate correction can be administered orally.

18. The device of claim 15, wherein each glucose measurement in the plurality of glucose measurements is autonomously measured and the plurality of fasting events are determined using the plurality of glucose measurements of the subject and the respective timestamps in the first data set.

19. The device of claim 15, wherein the identifying the single fasting event of the plurality of fasting events comprises identifying the first fasting period in the first time period encompassed by the time course by:

computing a moving period of variance $\sigma_k^2$ across the plurality of glucose measurements, wherein:

$$\sigma_k^2 = \frac{1}{M} \sum_{i=k-M+1}^{k} (G_i - \overline{G})^2$$

wherein, $G_i$ is the $i^{th}$ glucose measurement in a portion k of the plurality of glucose measurements, M is a number of glucose measurements in the plurality of glucose measurements and represents a contiguous predetermined time span, $\overline{G}$ is the mean of the glucose measurements selected from the plurality of glucose measurements, and k is within the first time period; and associating the first fasting period with a period of minimum variance $$\min_k \sigma_k^2$$

within the first time period.

20. The device of claim 15, wherein the identifying the single fasting event of the plurality of fasting events comprises receiving an indication of each fasting event in the plurality of fasting events from the subject.

21. The device of claim 15, wherein the identifying the single fasting event of the plurality of fasting events comprises receiving a second data set from a wearable device worn by the subject, and the second data set indicates a physiological metric of the user during the time course that is indicative of the plurality of fasting events.

22. The device of claim 15, the method further comprising:

obtaining a third data set from one or more insulin pens used by the subject to apply the standing insulin regimen, the third data set comprising a plurality of insulin medicament records, each insulin medicament record in the plurality of medicament records comprising: (i) a respective insulin medicament injection event including an amount of insulin medicament injected into the subject using a respective insulin pen in the one or more insulin pens, (ii) a corresponding insulin event electronic timestamp that is automatically generated by the respective insulin pen upon occurrence of the respective insulin medicament injection event, and (iii) a respective type of insulin medicament injected into the subject from one of (a) the basal insulin medicament and (b) the bolus insulin medicament, and using the third data set to exclude fasting events from the plurality of fasting events that do not occur within a first predetermined time interval after a bolus injection event or within a second predetermined time interval after a basal injection event.

23. The device of claim 1, wherein the plurality of fasting events are within the last week, within the last two weeks, or within the last month and wherein the method is repeated on a recurring basis over time.

24. The device of claim 15, wherein a determination is made to make the recommended adjustment to the basal/bolus ratio for the subject, and the adjustment is between 1 and 5 percent of the initial basal/bolus ratio, between 5 and 10 percent of the initial basal/bolus ratio, or between 10 and 15 percent of the initial basal/bolus ratio.

25. The device of claim 1, wherein the device further comprises a wireless receiver, and the first data set is obtained wirelessly from a glucose sensor affixed to the subject.

26. The device of claim 15, wherein
the basal insulin medicament consists of a single insulin medicament having a duration of action that is between 12 and 24 hours or a mixture of insulin medicaments that collectively have a duration of action that is between 12 and 24 hours, and
the bolus insulin medicament consists of a single insulin medicament having a duration of action that is between three to eight hours or a mixture of insulin medicaments that collectively have a duration of action that is between three to eight hours.

27. A method for adjusting a basal/bolus ratio in a standing insulin regimen for a subject, the method comprising performing, with
a computer system comprising one or more processors and a memory, steps of:
obtaining the standing insulin regimen for the subject, wherein
the standing insulin regimen is specific for the subject and comprises a daily total insulin medicament,
the daily total insulin medicament is satisfied by a combination of a daily amount of a basal insulin medicament and a daily amount of a bolus insulin medicament specified by the standing insulin regimen for the subject that is administered by one or more insulin pens, and
the daily amount of basal insulin medicament and the daily amount of bolus insulin medicament defines an initial basal/bolus ratio between the daily amount of basal insulin medicament and the daily amount of bolus insulin medicament;
determining and storing the initial basal/bolus ratio;
obtaining a first data set, the first data set comprising a plurality of glucose measurements of the subject over a time course, wherein the time course encompasses a first fasting period in a first time period, and, for each respective glucose measurement in the plurality of glucose measurements, a timestamp representing when the respective measurement was made;
identifying a single fasting event of a plurality of fasting events in the first fasting period of the time course;
computing iteratively, for the single fasting event, a minimum temporal glucose gradient uniquely associated with the single fasting event using the glucose measurements of the subject obtained from the first data set that are in the first fasting period of the single fasting event;
using the minimum gradient of the single fasting event to make a recommended adjustment to the standing insulin regimen by controlling the basal/bolus ratio for the subject while maintaining the daily total insulin medicament at a constant level,
wherein the using the minimum gradient of the single fasting event to determine whether to make a recommended adjustment to the basal/bolus ratio for the subject while maintaining the daily total insulin medicament comprises:
defining or accessing a positive threshold and a negative threshold,
deeming the standing insulin regimen for the subject basal deficient when the gradient of the single fasting event is positive and exceeds a positive threshold,
deeming the standing insulin regimen for the subject is bolus deficient when the gradient of the single fasting event is negative and exceeds a negative threshold, and
otherwise, deeming the standing insulin regimen for the subject basal/bolus ratio sufficient;
in response to deeming the standing insulin regimen for the subject basal deficient, communicating the recommended adjustment to the basal/bolus ratio, to make the recommended adjustment to the basal/bolus ratio for the subject, to:
(i) the subject for manual adjustment of the basal/bolus ratio in the standing insulin regimen,
(ii) each insulin pen in the one or more insulin pens charged with delivering the standing insulin regimen to the subject, as dosage adjustment instructions, or
(iii) a health care practitioner associated with the subject; and
controlling the one or more insulin pens to administer, by the one or more insulin pens, at least one dose of an adjusted standing insulin regimen based on the recommended adjustment.

28. A non-transitory computer-readable data carrier having stored thereon a computer program configured to cause a computer system comprising one or more processors and a memory to execute steps of:
obtaining the standing insulin regimen for the subject, wherein
the standing insulin regimen is specific for the subject and comprises a daily total insulin medicament,
the daily total insulin medicament is satisfied by a combination of a daily amount of a basal insulin medicament and a daily amount of a bolus insulin medicament specified by the standing insulin regimen for the subject that is administered by one or more insulin pens, and
the daily amount of basal insulin medicament and the daily amount of bolus insulin medicament defines an initial basal/bolus ratio between the daily amount of basal insulin medicament and the daily amount of bolus insulin medicament;
determining and storing the initial basal/bolus ratio;
obtaining a first data set, the first data set comprising a plurality of glucose measurements of the subject over a time course, wherein the time course encompasses a first fasting period in a first time period, and, for each respective glucose measurement in the plurality of glucose measurements, a timestamp representing when the respective measurement was made;
identifying a single fasting event of a plurality of fasting events in the first fasting period of the time course;
computing iteratively, for the single fasting event, a minimum temporal glucose gradient uniquely associated with the single fasting event using the glucose measurements of the subject obtained from the first data set that are in the first fasting period of the single fasting event;
using the minimum gradient of the single fasting event to make a recommended adjustment to the standing insulin regimen by controlling the basal/bolus ratio for the subject while maintaining the daily total insulin medicament at a constant level,
wherein the using the minimum gradient of the single fasting event to determine whether to make a recommended adjustment to the basal/bolus ratio for the subject while maintaining the daily total insulin medicament comprises:
defining or accessing a positive threshold and a negative threshold, deeming the standing insulin regimen for the subject basal deficient when the gradient of the single fasting event is positive and exceeds a positive threshold, deeming the standing insulin regimen for the subject is bolus deficient when the gradient of the single fasting event is negative and exceeds a negative threshold, and otherwise, deeming the standing insulin regimen for the subject basal/bolus ratio sufficient;

in response to deeming the standing insulin regimen for the subject basal deficient, communicating the recommended adjustment to the basal/bolus ratio, to make the recommended adjustment to the basal/bolus ratio for the subject, to:

(i) the subject for manual adjustment of the basal/bolus ratio in the standing insulin regimen, (ii) each insulin pen in the one or more insulin pens charged with delivering the standing insulin regimen to the subject, as dosage adjustment instructions, or (iii) a health care practitioner associated with the subject; and controlling the one or more insulin pens to administer, by the one or more insulin pens, at least one dose of an adjusted standing insulin regimen based on the recommended adjustment.

* * * * *